(12) United States Patent
Trifiro et al.

(10) Patent No.: US 12,624,386 B2
(45) Date of Patent: May 12, 2026

(54) ULTRAVIOLET QUANTITATIVE LABEL-FREE DETECTION OF DNA AMPLIFICATION

(71) Applicant: THE ROYAL INSTITUTION FOR THE ADVANCEMENT OF LEARNING/MCGILL UNIVERSITY, Montreal (CA)

(72) Inventors: Mark Trifiro, Montreal (CA); Ngoc Anh Minh Tran, Montreal (CA); Miltiadis Paliouras, Laval (CA); Andrew Kirk, Outremont (CA); Seung Soo Lee, Cheonan-Si (KR); Padideh Mohammadyousef, Verdun (CA)

(73) Assignee: The Royal Institution for the Advancement of learning/McGill University, Montréal (CA)

( * ) Notice: Subject to any disclaimer, the term of this patent is extended or adjusted under 35 U.S.C. 154(b) by 1194 days.

(21) Appl. No.: 17/413,216

(22) PCT Filed: Dec. 13, 2019

(86) PCT No.: PCT/CA2019/051805
§ 371 (c)(1),
(2) Date: Jun. 11, 2021

(87) PCT Pub. No.: WO2020/118444
PCT Pub. Date: Jun. 18, 2020

(65) Prior Publication Data
US 2022/0056514 A1 Feb. 24, 2022

Related U.S. Application Data

(60) Provisional application No. 62/779,132, filed on Dec. 13, 2018.

(51) Int. Cl.
| | | |
|---|---|---|
| *C12Q 1/6851* | (2018.01) | |
| *B01L 7/00* | (2006.01) | |
| *G01N 21/33* | (2006.01) | |

(52) U.S. Cl.
CPC .............. *C12Q 1/6851* (2013.01); *B01L 7/52* (2013.01); *G01N 21/33* (2013.01); *B01L 2300/18* (2013.01); *B01L 2300/1861* (2013.01)

(58) Field of Classification Search
None
See application file for complete search history.

(56) References Cited

U.S. PATENT DOCUMENTS

| | | | |
|---|---|---|---|
| 7,430,231 B2 | 9/2008 | Luo et al. | |
| 7,943,305 B2* | 5/2011 | Korlach | C12Q 1/6869 435/6.12 |

(Continued)

FOREIGN PATENT DOCUMENTS

| | | |
|---|---|---|
| EP | 2481817 | 8/2012 |
| WO | WO2015/006864 A1 | 1/2015 |
| WO | 2013113910 | 8/2018 |

OTHER PUBLICATIONS

Link, S. et al., "Shape and size dependence of radiative, non-radiative and pholothermal properties of gold nanocrystals," Int. Rev. Phys. Chem. 2000, vol. 19(3), p. 409-453.

(Continued)

*Primary Examiner* — Brian R Gordon
(74) *Attorney, Agent, or Firm* — Decode Legal Inc.; Mathieu Miron

(57) ABSTRACT

The present document describes methods and systems for amplifying and quantifying amplification of a nucleic acid molecule, with a polymerase chain reaction (PCR) or a loop-mediated isothermal amplification (LAMP), by irradiating, with a heating activation light beam from a continuous wave laser a biological enzymatic reaction mixture in solu- (Continued)

tion comprising a nucleic acid template, a polymerase enzyme, and chemically modified nanoparticles. Quantification of the amplification is achieved by irradiating the biological enzymatic reaction mixture during an annealing and/or elongation steps with an ultraviolet (UV) light source and measuring with a photodetector a transmission change in UV light transmission.

15 Claims, 27 Drawing Sheets

(56)                    References Cited

U.S. PATENT DOCUMENTS

| | | | | |
|---|---|---|---|---|
| 7,998,672 | B2 | 8/2011 | Roper | |
| 8,232,091 | B2 | 7/2012 | Maltezos et al. | |
| 9,816,132 | B2 | 11/2017 | Roche | |
| 12,162,008 | B2 * | 12/2024 | Colston, Jr. ....... | B01L 3/502715 |
| 12,168,231 | B2 * | 12/2024 | Colston, Jr. ........... | G01N 21/49 |
| 2003/0186240 | A1 * | 10/2003 | Su ........................ | C12Q 1/6869 435/6.1 |
| 2006/0166249 | A1 * | 7/2006 | Rothberg ............. | C12Q 1/6816 977/924 |
| 2008/0131939 | A1 | 6/2008 | Roper | |
| 2010/0330578 | A1 * | 12/2010 | Duhr ................... | B01L 3/50273 422/82.08 |
| 2014/0127695 | A1 * | 5/2014 | Drake ................. | C12Q 1/6816 435/6.12 |
| 2014/0377764 | A1 * | 12/2014 | Stehr ...................... | B82Y 20/00 435/6.12 |
| 2017/0037454 | A1 * | 2/2017 | Stehr ...................... | C12Q 1/686 |
| 2018/0044715 | A1 * | 2/2018 | Iyidogan .............. | C12Q 1/6806 |
| 2018/0237824 | A1 * | 8/2018 | Buersgens ........... | C12Q 1/6851 |
| 2019/0112650 | A1 * | 4/2019 | Ju ........................... | B82Y 5/00 |
| 2025/0137929 | A1 * | 5/2025 | Zhao ................ | G01N 33/54346 |

OTHER PUBLICATIONS

Deng, H. et al., "Gold nanoparticles with asymmetric polymerase chain reaction for colorimetric detection of DNA sequence," Analytical Chemistry, vol. 84, p. 1253-1258, Jan. 13, 2012.

Roper, D.K. et al., "Microscale heat transfer transduced by surface plasmon resonant gold nanoparticles," J_ Phys, :; hem C Nanomaler Interfaces, vol. 111 (9), p. 3636-3641, Sep. 2007.

Sipova, H. et al., "Surface plasmon resonance sensing of nucleic acids: A review," Analytica Chimica Acta, vol. 773, p. 9-23, Apr. 22, 2013.

Roche, Philip et al., Demonstration of a plasmonic Ihermocycler for the amplification of human androgen receptor DNA, Analyst, 2012. pp. 4475-4481, 137, The Royal society of Chemistry, UK.

Huang, Yi-You et al., A protein detection technique by using surface plasmon resonance {SPR} with rolling circle amplificalion {RCA} and nanogold-modified tags, Biosensors and Bioelectronics, 2007 , pp. 980-985, 22, Elsevier B.V., Philadelphia.

Xiang, Yang et al., Isothermal detection of multiple point mutations by a surface plasmon resonance biosensor with Au nanoparticles enhanced surface-anchored rolling circle amplification, Biosensors and Bioelectronics, 2013, pp. 142-449, 49, Elsevier B.V., Philadelphia.

Polo, Ester et al., Plasmonic-driven thermal sensing: ultralow detection of cancer markers, Chem. Commun., 2013, pp. 3676-3678,49, The Royal Society of Chemistry, UK.

Richardson, H. H., Carlson, M. T., Tandler, P. J., Hernandez, P., & Govorov, A.O. (2009). Experimental theoretical studies of light-to-heat conversion and collective healing effects in metal nanoparticle solutions. Nano letters, 9(3), 1139-1146.

Li M, Lin YC, Wu CC, Liu HS. Enhancing the efficiency of a PCR using gold nanoparticles. Nucleic Acids Res. Nov. 27, 2005;33(21):1-10.

Li H, Huang J, Lv J, An H, Zhang X, Zhang Z, Fan C, Hu J. Nanoparticle PCR: nanogold-assisted PCR with enhanced specificity. Angew Chem Int Ed Engl. Aug. 12, 2005; 44(32):5100-3.

Akilany, A. M., & Murphy, C.J. (2010). Toxicity and cellular uptake of gold nanoparticles: what we have learned so far?. Journal of nanoparticle research, 12(7), 2313-2333.

Belder D, Ludwig M. Surface modification in microchip electrophoresis. Electrophoresis. Nov. 2003; 24(21 ):3595-606. Review.

Jain PK, Huang X, El-Sayed IH, El-Sayed MA. Noble metals on the nanoscale: optical and photothermal properties and some applications in imaging, sensing, biology, and medicine. Ace Chem Res. Dec. 2008 41(12):1578-86.

Jain, P.K., Huang, X., El-Sayed, I.H., & El-Sayed, M. A. Review of some interesting surface plasmon resonance-enhanced properties of noble metal nanoparticles and their applications to biosystems. Plasmonics, 2007, 2(3), 107-118.

Hrelescu, C., Stehr, J., Ringler, M., Sperling, R. A., Parak, W.J., Klar, T.A., & Feldman, J. (2010). DNA melting in gold nanostove clusters. The Journal of Physical Chemistry C, 114(16), 7401-7411.

Lassiter JB, Knight MW, Mirin NA, Halas NJ. Reshaping the plasmonic properties of an individual nanoparticle. Nano Lett. Dec. 2009;9(12):4326-32.

Lee, K.S., & El-Sayed, M.A. (2006). Gold and silver nanoparticles in sensing and imaging: sensitivity of plasmon response to size, shape, and metal composition. The journal of Physical Chemistry B, 110(39), 19220-19225.

Lou, X., & Zhang, Y. (2013). Mechanism studies on nanoPCR and applications of gold nanoparticles in genetic analysis. ACS applied materials & interfaces, 5(13), 6276-6284.

Pissuwan D, Valenzuela S, Cortie MB. Prospects for gold nanorod particles in diagnostic and therapeutic applications. Biotechnol Genet Eng Rev. 2008; 25: 93-112. Review.

Stehr J, Hrelescu C, Sperling RA, Raschke G, Wunderlich M, Nichtl A, Heindl D, Kurzinger K, Parak WJ, Klar TA, Feldmann J. Gold nanostoves for microsecond DNA melting analysis. Nano Lett. Feb. 2008; 8(2):619-23. Epub Jan. 26, 2008.

Warshavski, O., Minai, L., Bisker, G., & Yelin, D. (2011). Effect of single femtosecond pulses on gold nanoparticles. The Journal of Physical Chemistry C, 115(10), 3910-3917.

Xia, Y. M., Hua, Z. S., Srivannavil, O., Ozel, A. B., & Gulari, E. (2007). Minimizing the surface effect of PDMS-glass microchip on polymerase chain reaction by dynamic polymer passivation. Journal of Chemical Technology and Biotechnology, 82(1), 33-38.

Fang, C., Shao, L., Zhao, Y., Wang, J., & Wu, H. A gold nanocrystal/poly(dimethylsiloxane) composite for plasmonic healing on microfluidic chips. Advanced Materials, 2012. 24(1):94-98.

Miyako, E., Nagata H., Hirano, K., Makita, Y., Nakayama, K.I., & Hirotsu, T. Near-infared laser-triggered carbon nanohorns for selective elimination of microbes. Nanotechnology, 2007. 18(47), 475103.

Miyako, Eijiro, et al. Carbon Nanolube-Polymer Composite for Light-Driven Microthermal Control. Angewandle Chemie International Edition. 2008. 47(19) 3610-3613.

2008—Supporting info for Miyako, Eijiro, et al. Carbon Nanotube-Polymer Composite for Light-Driven Microthermal Control. Angewandte Chemie International Edition. 2008. 47(19) 3610-3613.

Miyako, Eijiro, Hideya Nagata, Ken Hirano, and Takahiro Hirotsu. Laser-triggered carbon nanotube microdevice for remote control of biocatalyctic reactions. Lab on a chip. 2009. 9(6): 788-794.

Li Z, Wang P, Tong L, Zhang L. Gold nanorod-facilitated localized healing of droplets in microfluidic chips. Opt Express. Jan. 14, 2013; 21(1):1281-6.

Sun, Xiaohong, Qian Xu, Yingjie Pan, Weiqing Lan, Yong Zhao, and Vivian CH Wu. A loop-mediated isothermal amplification method for rapid detection of Vibrio parahaemolyticus in seafood. Annals of microbiology, 2012, 62(1): 263-271 (Year: 2012).

Bedford EE, Spadavecchia J, Pradier CM, Gu FX. Surface plasmon resonance biosensors incorporating gold nanoparticles. Macromol Biosci. Jun. 2012; 12(6):724-39. Epub Mar. 13, 2012. (Year: 2012).

Cai, M., Li, F., Zhang, Y. and Wang, Q., One-pot polymerase chain reaction with gold nanoparticles for rapid and ultrasensitive DNA detection. Nano Research, 2010, 3(8):557-563. (Year: 2010).

(56) References Cited

OTHER PUBLICATIONS

Gao, Xiang, Qingdai Liu, Yi Zhao, Zhenjing Li, Yurong Wang, Dongsheng Zhou, Kan Jiang, and Cheng Luo. Influences of gold and silver nanoparticles in loop-mediated isothermal amplification reactions. Journal of Experimental Nanoscience 9, 2014, (9): 922-930 . Epub Dec. 10, 2012. (Year: 2012).

Mi, Li Juan, Hong Ping Zhu, XiaoDong Zhang, Jun Hu, and Chun Hai Fan. Mechanism of the interaction between Au nanoparticles and polymerase in nanoparticle PCR. Chinese Science Bulletin 2007, 52(17): 2345-2349. (Year: 2007).

Notomi T, Okayama H, Mashubuchi H, Yonekawa T, Watanbe K, Amino N, Hase T. Loop-mediated isothermal amplification of DNA. Nucleic Acids Res. Jun. 15, 2000; 28(12): E63, Not in Eng. pp. 236-237, (Year: 2000).

Imai M, Ninomiya A, Minekawa H, Notomi T, Ishizaki T, Tashiro M, Odagiri T. Development of H5-RT-LAMP (loop-mediated isothermal amplification) system for rapid diagnosis of H5 avian influenza virus infection. Vaccine. Nov. 10, 2006; 24(44-46):6679-82. Epub Jun. 8, 2006. (Year: 2006).

Arunrut N, Seetang-Nun Y, Phromjai J, Panphut W, Kiatpathomichai W. Rapid and sensitive detection of Laem-Singh virus by reverse transcription loop-mediated isothermal amplification combined with a lateral flow dipstick. J Virol Methods. Oct. 2011; 177(1): 71-4. Epub Jul. 5, 2001. (Year 2011).

International Search Report and Written Opinion issued on Mar. 18, 2021 in international stage.

Tran, N.A.M. "Universal point of care biosensor using ultrafast plasmonic polymerase chain reaction". McGill University Thesis, Jan. 19, 2018.

Uchehara, G. "Real time label free monitoring of plasmonic polymerase chain reaction products". McGill University Thesis, Aug. 2018.

Roche, P.J.R, et al., "Real time plasmonic qPCR: how fast is ultra-fast? 30 cycles in 54 seconds". Analyst, 2017, vol. 142(10), pp. 1746-1755.

Supplementary European Search Report from Corresponding European Application No. 19897469.3; Munich; Bradbrook, Derek; Aug. 30, 2022.

Lee Jung-Hoon et al., "Plasmonic Photothermal Gold Bipyramid Nanoreactors for Ultrafast Real-Time Bioassays", Journal of the American Chemical Society, vol. 139, No. 24, doi:10.1021/jacs. 7b01779, ISSN 0002-7863, (Jun. 21, 2017), pp. 8054-8057, URL: https://pubs.acs.org/doi/pdf/10.1021/jacs.7b01779.

Uchehara et al., "Real time label-free monitoring of plasmonic polymerase chain reaction products", SPIE Proceedings; [Proceedings of SPIE ISSN 0277-786X], SPIE, US, (Mar. 27, 2019), vol. 10969, doi:10.1117/12.251829.

Mohammadyousef "Ultrafast Plasmonic and Real-Time Label-Free Polymerase Chain Reaction for Point-of-Care Diagnostics", ISBN 979-8-5442-2770-0, (Jan. 1, 2021), pp. 1-172, URL: https://www.proquest.com/dissertations-theses/ultrafast-plasmonic-real-time-label-free/docview/2596642338/se-2.

Mohammadyousef et al., "Plasmonic and label-free real-time quantitative PCR for point-of-care diagnostics", Analyst, UK, (Sep. 13, 2021), vol. 146, No. 18, doi:10.1039/D0AN02496A, ISSN 0003-2654.

Analyst (2017) 142:1746-1755, Roche et al.; Real time plasmonic qPCR is ultra-fast 30 cyclces in 54 seconds Biophysical Journal (2001) 81:3545-3559, Cherepanov et al.; Binding of Nucleotides by T4 DNA Ligase and T4 RNA Ligase: Optical Absorbance and Flourescence.

* cited by examiner (a) No delay (b) 200ms delay (c) 400ms delay (d) 800ms delay (a) No delay (b) 200ms delay (c) 400ms delay (d) 800ms delay (a) Annealing temperature varied from 52°C to 62°C.

(b) Annealing temperature varied from 60°C to 66°C.

(a) Annealing time variation with temperature kept at 60°C.

(b) Annealing time variation with temperature kept at 62°C.

(c) Annealing time variation with temperature kept at 64°C.

(a) Standard dNTP concentration 250μM (b) dNTP concentration 125μM (c) dNTP concentration 62.5μM (d) dNTP concentration 31.25μM (e) dNTP concentration 15.625μM (f) dNTP concentration 250μM, no DNA (a) Positive PCR (b)  Negative PCR, No DNA template

| VCSEL Parameters | Test Condition | Symbol | Min. | Typ. | Max. | Units | Notes |
|---|---|---|---|---|---|---|---|
| Optical Power Output | $I_F$=3.8A | Po | | 3 | | W | 2 |
| Threshold Current | | $I_{TH}$ | | 800 | | mA | |
| Slope Efficiency | Po =3.8W | η | | 1.1 | | mW/mA | 3 |
| Wall Plug Efficiency | $I_F$=3.8A | | | 40 | | % | |
| Emission Area | | | | 1100x1100 | | um | |
| Peak Wavelength | $I_F$=3.8A | $\lambda_P$ | | 808 | | nm | |
| Laser Forward Voltage | $I_F$=3.8A | $V_F$ | | - | | V | |
| Series Resistance | $I_F$=3.8A | $R_S$ | | 0.16 | | Ohms | |
| Beam Angle | $I_F$=3.8A | | | 20 | | Degrees | |

ULTRAVIOLET QUANTITATIVE LABEL-FREE DETECTION OF DNA AMPLIFICATION

CROSS-REFERENCE TO RELATED APPLICATIONS

This application claims priority of U.S. provisional patent No. 62/779,132 filed on Dec. 13, 2018, the specification of which is hereby incorporated by reference in its entirety.

BACKGROUND

(a) Field

The subject matter disclosed generally relates to methods and systems for amplifying nucleic acid molecules and quantifying amplification thereof. More specifically, the subject matter disclosed relates to methods and systems for amplifying nucleic acid molecules and quantifying amplification thereof with plasmonic heating and quantification of amplification with UV light transmission.

(b) Related Prior Art

DNA amplification technologies such as the polymerase chain reaction (PCR) and loop mediated amplification (LAMP) are methods widely used in molecular biology to make multiple copies of a specific DNA segment. Using PCR or LAMP, a single copy (or more) of a DNA sequence is exponentially amplified to generate thousands to millions of more copies of that particular DNA segment. For example, PCR is now a common and often indispensable technique used in medical laboratory and clinical laboratory research for a broad variety of applications including biomedical research and criminal forensics. Traditional PCR instruments commonly uses heating elements referred to as the Peltier block or element and relies on the contact of the sample tubes with the heating block to provide heating and cooling to the sample.

The advantages of Peltier elements are that the technology is well understood, thoroughly tested, and Peltier elements are readily available of-the-shelf at a low cost. One disadvantage of Peltier modules for use in PCR is that they are relatively slow when working with microliter reaction volumes, as the entire Peltier element, heat spreader and reaction sample's temperature must be changed at each cycle. The use of a water bath in conjunction with a robotic arm can be used to speed up the process. This, however, will increase cost, complexity and is certainly not a portable system. Moving to direct non-contact methods, such as plasmonic PCR, which rely on electromagnetic radiation as the mechanism for heat transfer, can potentially address the shortcomings of contemporary PCR machines. One caveat of these non-contact methods of heating is that the wall-plug efficiency is typically not 100%. As an example, lasers have a wall plug efficiency of about 40-50%.

DNA and other nucleic acids are regularly quantitated with PCR. Fluorescent labels can be added directly into the PCR mix to measures its fluorescent signal at each cycle. Fluorescent DNA-intercalating dyes such as ethidium bromide and SYBR™/Pico™ green are a simple and straightforward compound, which can be used in quantitative PCR (qPCR). In fact, the first qPCR assays employed ethidium bromide as a detection mechanism, as it also binds the double stranded DNA produced during amplification. However, concerns over safety and sensitivity of ethidium bromide led to the use of alternative fluorescent intercalating dyes, including SYBR™/Pico™ Green dye, in the qPCR reaction. Like ethidium bromide SYBR™/Pico™ Green preferentially binds to double-stranded DNA, but with a much greater affinity. The use of SYBR™ green and pico green has improved the sensitivity of detection meaning that fewer PCR cycles are required. These dyes are also far more quantitative, as the emission of fluorescence is directly proportional to the amount of PCR product generated. However, these dyes are costly and need to perpetually be added to the reaction mixture. Therefore, doing away with the addition of fluorescent labels would be advantageous.

Therefore, there is a need for methods of quantitating the production of DNA during DNA amplification reaction, or mitigating the disadvantages of currently existing methods for quantitating the production of DNA during DNA amplification reaction.

SUMMARY

According to an embodiment, there is provided a method of amplifying a nucleic acid molecule and quantify amplification thereof, with a polymerase chain reaction (PCR) or a loop-mediated isothermal amplification (LAMP), through bulk heating a biological enzymatic reaction mixture in solution containing a nucleic acid template, a polymerase enzyme, and chemically modified nanoparticles comprising nanorods of metal, having photo-thermal properties, to promote the PCR or the LAMP, comprising:

a) irradiating the chemically modified nanoparticles with an activation light beam from a continuous wave laser to provide excitation for a period of time to activate the photo-thermal properties of the chemically modified nanoparticles, such that the chemically modified nanoparticles release heat sufficient to provide the heating to the whole reaction mixture in solution and promote the PCR or the LAMP, and b) irradiating the biological enzymatic reaction mixture, during an annealing step, an elongation step, or both, with an ultraviolet (UV) light source and measuring a transmission change in UV light transmission therefrom to quantify amplification of the nucleic acid template, wherein the irradiating is for a duration and at an intensity sufficient to measure a free nucleotide concentration therein, while avoiding inhibition of amplification of the nucleic acid molecule.

The PCR may be a reverse transcriptase (RT) PCR, or the LAMP may be a RT LAMP.

The metal may be selected from the group consisting of Au, Ag, Pd, Pt, Fe, Cu, Al, and Zn.

The metal may be gold.

The nanoparticles may be gold nanorods.

The photo-thermal properties may comprise a localized plasmon resonance at a surface of the chemically modified nanoparticles, and the activation light beam has a wavelength corresponding to the localized plasmon resonance.

The chemically modified nanoparticles may be chemically modified by a chemical compound that prevents the inhibition of an active site of the polymerase enzyme.

The chemical compound that prevents the inhibition of the active site of the polymerase enzyme may be polyethylene glycol.

The step of irradiating may comprise adjusting a power of the activation light beam to regulate temperature of the biological enzymatic reaction mixture in solution through controlled heat release from the chemically modified nanoparticles.

The continuous wave laser may be a compact laser.

The compact laser may be a fibre-coupled laser, a vertical-cavity surface-emitting laser (VCSEL), or a combination thereof.

The compact laser may be a VCSEL.

The activation light beam from the compact laser may be provided from a distance of ≤5 mm from the biological enzymatic reaction mixture.

The activation light beam from the compact laser may be provided from a distance of from about 1 mm to about 5 mm from the biological enzymatic reaction mixture.

The activation light beam from the compact laser may be provided from a distance of from about 3 mm to about 5 mm from the biological enzymatic reaction mixture.

The activation light beam from the compact laser may be provided from a distance of about 5 mm from the biological enzymatic reaction mixture.

The method may further comprise a step of monitoring the bulk heating.

The monitoring the bulk heating may be performed with an infrared thermometer.

The monitoring may be during annealing step.

The monitoring may be during the elongation step.

The duration may be from about 10 ms to about 1000 ms, preferably 30 ms.

The intensity may be from about 0.5 to about 1 mW.

The UV light source may emit light having a wavelength of from about 175 nm to about 350 nm.

The UV light source may emit light having a wavelength of from about 240 nm to about 350 nm.

The UV light source may emit light having a wavelength of from about 260 nm to about 280 nm.

The UV light source may comprise a plurality of UV light source, configured to irradiate a plurality of nucleic acid sample.

The transmission change in UV light transmission may be measured with a photodetector.

The UV light from the UV light source may be focused through an optical lense, a light pipe, or a combination thereof.

The UV light from the UV light source may be focused through a light pipe onto the photodetector.

The method may be performed in real-time.

According to another embodiment, there is provided a system for performing a polymerase chain reaction (PCR) or a loop-mediated isothermal amplification (LAMP) of a nucleic acid molecule and quantify amplification thereof, the system comprising:

a) at least one nucleic acid sample containing a nucleic acid template, a polymerase enzyme, and chemically modified nanoparticles comprising nanorods of metal, having photo-thermal properties, to promote the PCR or the LAMP;

b) a thermal cycler in thermal communication with the at least one nucleic acid sample;

c) a continuous wave laser configured to irradiate the at least one nucleic acid sample and provide excitation for a period of time to activate the photo-thermal properties of the chemically modified nanoparticles;

d) an ultraviolet (UV) light source configured to irradiate the at least one nucleic acid sample;

e) a photodetector configured to measure the transmission changes in UV light absorbance from the at least one nucleic acid sample, f) a processor for analyzing the change transmission changes in UV light transmission and quantify amplification of the nucleic acid template.

The UV light source may be a UV light emitting diode (LED).

The UV light source may emit light having a wavelength of from about 175 nm to about 350 nm.

The UV light source may emit light having a wavelength of from about 240 nm to about 350 nm.

The UV light source may emit light having a wavelength of from about 260 nm to about 280 nm.

The system may comprise a plurality of UV light source, configured to irradiate a plurality of nucleic acid sample.

The system may comprise a plurality of photodetector, configured to measure absorbance from a plurality of nucleic acid sample.

The UV light from the UV light source may be focused through an optical lense, a light pipe, or a combination thereof.

The UV light from the UV light source may be focused through a light pipe onto the photodetector.

The metal may be selected from the group consisting of Au, Ag, Pd, Pt, Fe, Cu, Al, and Zn.

The metal may be gold.

The nanoparticles may be gold nanorods.

The photo-thermal properties may comprise a localized plasmon resonance at a surface of the chemically modified nanoparticles, and the activation light beam has a wavelength corresponding to the localized plasmon resonance.

The chemically modified nanoparticles may be chemically modified by a chemical compound that prevents the inhibition of an active site of the polymerase enzyme.

The chemical compound that prevents the inhibition of the active site of the polymerase enzyme may be polyethylene glycol.

The system may further comprise a thermometer for monitoring bulk heating of the at least one nucleic acid sample.

The thermometer may be an infrared thermometer.

The continuous wave laser may be a compact laser.

The compact laser may be a fibre-coupled laser, a vertical-cavity surface-emitting laser (VCSEL), or a combination thereof.

The compact laser may be a VCSEL.

The activation light beam from the compact laser may be provided from a distance of ≤5 mm from the biological enzymatic reaction mixture.

The activation light beam from the compact laser may be provided from a distance of from about 1 mm to about 5 mm from the biological enzymatic reaction mixture.

The activation light beam from the compact laser may be provided from a distance of from about 3 mm to about 5 mm from the biological enzymatic reaction mixture.

The activation light beam from the compact laser may be provided from a distance of about 5 mm from the biological enzymatic reaction mixture.

The system may provide real-time information about amplification of the nucleic acid template.

The PCR may be a reverse transcriptase (RT) PCR, or the LAMP may be a RT LAMP.

According to another embodiment, there is provided a method of amplifying a nucleic acid molecule, with a polymerase chain reaction (PCR) or a loop-mediated isothermal amplification (LAMP), through bulk heating a biological enzymatic reaction mixture in solution containing
    a nucleic acid template,
    a polymerase enzyme, and
    chemically modified nanoparticles comprising nanorods of metal, metallic coated organic nanotubes, or a combination thereof, having photo-thermal properties, to promote the PCR or the LAMP, comprising:
    a) irradiating the chemically modified nanoparticles with an activation light beam from a compact continuous wave laser to provide excitation for a period of time to activate the photo-thermal properties of the chemically modified nanoparticles, such that the chemically modified nanoparticles release heat sufficient to provide the heating to the whole reaction mixture in solution and promote the PCR or the LAMP.
    The method may further comprise step b):
    b) quantify amplification by irradiating the biological enzymatic reaction mixture, during an annealing step, an elongation step, or both, with an ultraviolet (UV) light source and measuring a transmission change in UV light transmission therefrom to quantify amplification of the nucleic acid template, wherein the irradiating is for a duration and at an intensity sufficient to measure a free nucleotide concentration therein, while avoiding inhibition of amplification of the nucleic acid molecule;
    wherein the chemically modified nanoparticles are nanorods of metal.
    The metallic coated organic nanotubes may be selected from the group consisting of carbon nanotubes coated with a metal and multiwalled carbon nanotubes coated with or decorated with a metal.
    The metal may be selected from the group consisting of Au, Ag, Pd, Pt, Fe, Cu, Al, and Zn.
    The metal may be gold.
    The nanoparticles may be gold nanorods.
    The photo-thermal properties may comprise a localized plasmon resonance at a surface of the chemically modified nanoparticles, and the activation light beam has a wavelength corresponding to the localized plasmon resonance.
    The chemically modified nanoparticles may be chemically modified by a chemical compound that prevents the inhibition of an active site of the polymerase enzyme.
    The chemical compound that prevents the inhibition of the active site of the polymerase enzyme may be polyethylene glycol.
    The step of irradiating may comprise adjusting a power of the activation light beam to regulate temperature of the biological enzymatic reaction mixture in solution through controlled heat release from the chemically modified nanoparticles.
    The compact continuous wave laser may be a fibre-coupled laser, a vertical-cavity surface-emitting laser (VCSEL), or a combination thereof.
    The compact laser may be a VCSEL.
    The activation light beam from the compact continuous wave laser may be provided from a distance of ≤5 mm from the biological enzymatic reaction mixture.
    The activation light beam from the compact continuous wave laser may be provided from a distance of from about 1 mm to about 5 mm from the biological enzymatic reaction mixture.
    The activation light beam from the compact continuous wave laser may be provided from a distance of from about 3 mm to about 5 mm from the biological enzymatic reaction mixture.

The activation light beam from the compact continuous wave laser may be provided from a distance of about 5 mm from the biological enzymatic reaction mixture.
    The method may further comprise a step of monitoring the bulk heating.
    The monitoring the bulk heating may be performed with an infrared thermometer.
    The monitoring may be during annealing step.
    The monitoring may be during the elongation step.
    The duration may be from about 10 ms to about 1000 ms, preferably 30 ms.
    The intensity may be from about 0.5 to about 1 mW.
    The UV light source may emit light having a wavelength of from about 175 nm to about 350 nm.
    The UV light source may emit light having a wavelength of from about 240 nm to about 350 nm.
    The UV light source may emit light having a wavelength of from about 260 nm to about 280 nm.
    The UV light source may comprise a plurality of UV light source, configured to irradiate a plurality of nucleic acid sample.
    The transmission change in UV light transmission may be measured with a photodetector.
    The UV light from the UV light source may be focused through an optical lense, a light pipe, or a combination thereof.
    The UV light from the UV light source may be focused through a light pipe onto the photodetector.
    The method may be performed in real-time.
    According to another embodiment, there is provided a system for performing a polymerase chain reaction (PCR) or a loop-mediated isothermal amplification (LAMP) of a nucleic acid molecule, the system comprising:
    a) at least one nucleic acid sample containing
    a nucleic acid template,
    a polymerase enzyme, and
    chemically modified nanoparticles comprising nanorods of metal, metallic coated organic nanotubes, or a combination thereof, having photo-thermal properties, to promote the PCR or the LAMP;
    b) a thermal cycler in thermal communication with the at least one nucleic acid sample; and
    c) a compact continuous wave laser configured to irradiate the at least one nucleic acid sample and provide excitation for a period of time to activate the photo-thermal properties of the chemically modified nanoparticles.
    The system may further comprise:
    d) an ultraviolet (UV) light source configured to irradiate the at least one nucleic acid sample;
    e) a photodetector configured to measure the transmission changes in UV light absorbance from the at least one nucleic acid sample, and
    f) a processor for analyzing the change transmission changes in UV light transmission and quantify amplification of the nucleic acid template;
    wherein the chemically modified nanoparticles are nanorods of metal,
    for quantifying amplification of the nucleic acid.
    The UV light source may be a UV light emitting diode (LED).
    The UV light source may emit light having a wavelength of from about 175 nm to about 350 nm.
    The UV light source may emit light having a wavelength of from about 240 nm to about 350 nm.
    The UV light source may emit light having a wavelength of from about 260 nm to about 280 nm.

The system may comprise a plurality of UV light source, configured to irradiate a plurality of nucleic acid sample.

The system may comprise a plurality of photodetector, configured to measure absorbance from a plurality of nucleic acid sample.

The UV light from the UV light source may be focused through an optical lense, a light pipe, or a combination thereof.

The UV light from the UV light source is focused through a light pipe onto the photodetector.

The metallic coated organic nanotubes may be selected from the group consisting of carbon nanotubes coated with a metal and multiwalled carbon nanotubes coated with or decorated with a metal.

The metal may be selected from the group consisting of Au, Ag, Pd, Pt, Fe, Cu, Al, and Zn.

The metal may be gold.

The nanoparticles may be gold nanorods.

The photo-thermal properties may comprise a localized plasmon resonance at a surface of the chemically modified nanoparticles, and the activation light beam has a wavelength corresponding to the localized plasmon resonance.

The chemically modified nanoparticles may be chemically modified by a chemical compound that prevents the inhibition of an active site of the polymerase enzyme.

The chemical compound that prevents the inhibition of the active site of the polymerase enzyme may be polyethylene glycol.

The system may further comprise a thermometer for monitoring bulk heating of the at least one nucleic acid sample.

The thermometer may be an infrared thermometer.

The compact continuous wave laser may be a fibre-coupled laser, a vertical-cavity surface-emitting laser (VC-SEL), or a combination thereof.

The compact laser may be a VCSEL.

The activation light beam from the compact laser may be provided from a distance of ≤5 mm from the biological enzymatic reaction mixture.

The activation light beam from the compact laser may be provided from a distance of from about 1 mm to about 5 mm from the biological enzymatic reaction mixture.

The activation light beam from the compact laser may be provided from a distance of from about 3 mm to about 5 mm from the biological enzymatic reaction mixture.

The activation light beam from the compact laser may be provided from a distance of about 5 mm from the biological enzymatic reaction mixture.

The system may provide real-time information about amplification of the nucleic acid template.

In the method of the present invention, the PCR may be a reverse transcriptase (RT) PCR, or the LAMP may be a RT LAMP.

In the system of the present invention, PCR may be a reverse transcriptase (RT) PCR, or the LAMP may be a RT LAMP.

The following terms are defined below.

The term "nucleic acid" is intended to mean the biopolymers, or small biomolecules, essential to all known forms of life. The term nucleic acid is the overall name for DNA and RNA. They are composed of nucleotides, which are the monomers made of three components: a 5-carbon sugar, a phosphate group and a nitrogenous base (adenine, thymine, guanine and cytosine). If the sugar is a compound ribose, the polymer is RNA (ribonucleic acid); if the sugar is derived from ribose as deoxyribose, the polymer is DNA (deoxyribonucleic acid). As used herein, the term is meant to encompass all forms of nucleic acid that may be used or that may be obtained for use in a PCR or LAMP reaction. This includes genomic DNA, RNA, mRNA, rRNA, reversed transcribed RNA, cDNA.

The terms "polymerase chain reaction" or "PCR" are intended to mean the method used in molecular biology to make multiple copies of a specific DNA segment. Using PCR, a single copy (or more) of a DNA sequence is exponentially amplified to generate thousands to millions of more copies of that particular DNA segment. It may be combined with a reverse transcription step to allow the detection of RNA (i.e. RT-PCR).

The terms "loop mediated isothermal amplification" or "LAMP" is a single tube technique for the amplification of DNA. In contrast to the PCR in which the reaction is carried out with a series of alternating temperature steps or cycles, isothermal amplification is carried out at a constant temperature, and does not require a thermal cycler. It may be of use to detect certain diseases. It may be combined with a reverse transcription step to allow the detection of RNA.

The terms "power conversion efficiency" or "wall plug efficiency" of a laser are intended to mean the ratio between its optical output power to consumed electrical input power.

The term "slope efficiency" is intended to mean a slope of the curve obtained by plotting the laser output versus the pump power.

Features and advantages of the subject matter hereof will become more apparent in light of the following detailed description of selected embodiments, as illustrated in the accompanying figures. As will be realized, the subject matter disclosed and claimed is capable of modifications in various respects, all without departing from the scope of the claims. Accordingly, the drawings and the description are to be regarded as illustrative in nature, and not as restrictive and the full scope of the subject matter is set forth in the claims.

BRIEF DESCRIPTION OF THE DRAWINGS

Further features and advantages of the present disclosure will become apparent from the following detailed description, taken in combination with the appended drawings, in which.

It will be noted that throughout the appended drawings, like features are identified by like reference numerals.

DETAILED DESCRIPTION

Figure 1:
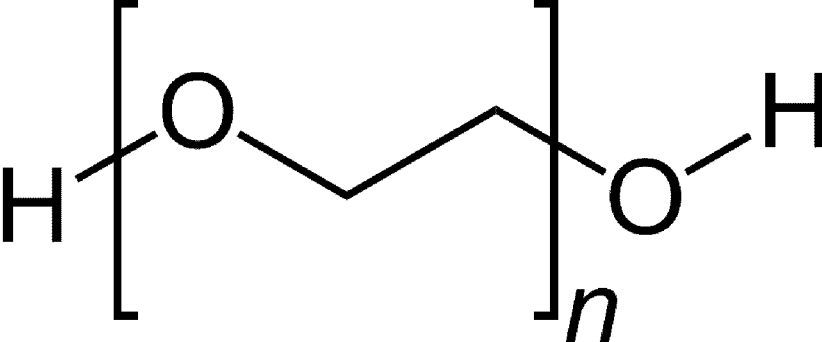
FIG. 1 illustrates the molecular structure of polyethylene glycol.

In embodiments there is disclosed a method of amplifying a nucleic acid molecule and quantify amplification thereof, with a polymerase chain reaction (PCR) or a loop-mediated isothermal amplification (LAMP), through bulk heating a biological enzymatic reaction mixture in solution. The biological enzymatic reaction mixture contains a nucleic acid template, a polymerase enzyme, and chemically modified nanoparticles comprising nanorods of metal, having photo-thermal properties, to promote the PCR or the LAMP.

The method comprises the steps of:

a) irradiating the chemically modified nanoparticles with an activation light beam from a continuous wave laser to provide excitation for a period of time to activate the photo-thermal properties of the chemically modified nanoparticles, such that the chemically modified nanoparticles release heat sufficient to provide the heating to the whole reaction mixture in solution and promote the PCR or the LAMP, and b) irradiating the biological enzymatic reaction mixture, during an annealing step, an elongation step, or both, with an ultraviolet (UV) light source and measuring a change in UV light transmission therefrom to quantify amplification of the nucleic acid template, wherein the irradiating is for a duration and at an intensity sufficient to measure a free nucleotide concentration therein, while avoiding inhibition of amplification of the nucleic acid molecule.

In accordance with another embodiment, there is disclosed a method of amplifying a nucleic acid molecule, with a polymerase chain reaction (PCR) or a loop-mediated isothermal amplification (LAMP), through bulk heating a biological enzymatic reaction mixture in solution containing a nucleic acid template, a polymerase enzyme, and chemically modified nanoparticles comprising nanorods of metal, metallic coated organic nanotubes, or a combination thereof, having photo-thermal properties, to promote the PCR or the LAMP, comprising irradiating the chemically modified nanoparticles with an activation light beam from a compact continuous wave laser to provide excitation for a period of time to activate the photo-thermal properties of the chemically modified nanoparticles, such that the chemically modified nanoparticles release heat sufficient to provide the heating to the whole reaction mixture in solution and promote the PCR or the LAMP.

The methods may also include a step of quantifying amplification of the nucleic acid by irradiating the biological enzymatic reaction mixture, during an annealing step, an elongation step, or both, with an ultraviolet (UV) light source and measuring a transmission change in UV light transmission therefrom to quantify amplification of the nucleic acid template, wherein irradiating is for a duration and at an intensity sufficient to measure a free nucleotide concentration therein, while avoiding inhibition of amplification of the nucleic acid molecule, wherein the chemically modified nanoparticles are nanorods of metal.

Ultraviolet Light Source

In embodiments, the UV light source may emit light having a wavelength of from about 175 nm to about 350 nm, or having a wavelength of from about 240 nm to about 350 nm, or having a wavelength of from about 260 nm to about 280 nm. In embodiments, the absorption of nucleic acid at 260 nm decreases when going from free floating nucleotide to double stranded DNA. Due to base stacking of the nucleotide limiting the resonance of the heterocyclic rings. By tracking the changes in transmission, one can track the process of free-floating nucleotide forming double stranded DNA, and thus amplicon production.

According to some embodiments, the UV light source may comprise a plurality of UV light source, configured to irradiate a plurality of nucleic acid sample.

Any suitable source of UV light may be used. UV light emitting diodes are well suited for this task.

According to another embodiment, the UV light from the UV light source may be focused through an optical lense, a light pipe, or a combination thereof. The optical lense and light pipe may contribute to provide a highly sensitive DNA detection system even for minimal optical intensity changes at the photodetector.

Heating Mechanism and Nanoparticles

The method of heating a DNA template according to embodiments of the invention generally includes the steps of contacting the reaction mixture containing the DNA template with nanoparticles having photo-thermal properties, and irradiating the nanoparticles using an activation light beam activating these photo-thermal properties, such that the nanoparticles release heat sufficient to provide the desired heating. In effect, instead of using Peltier heaters or infrared lamps to transfer heat to the vessel containing the reaction mixture, embodiments of the invention use nanoparticles as "heaters".

The nanoparticles may be embodied by any particles of nanometric dimensions capable to release heat upon optical stimulation. Nanometer-sized particles are often defined as particles with at least one dimension below 100 nm. Particles not meeting this threshold, but still of a small enough size to exhibit properties typically associated with nanoparticles, may however still be considered within the scope of the present invention. The nanoparticles may for example be embodied by nanospheres or nanorods made of a metal such as gold, silver or the like, carbon nanotubes coated with a metal or multiwalled carbon nanotubes (MWCNT) coated with or decorated with a metal, and the like. The metal may for example be Gold (Au), Silver (Ag), Palladium (Pd), Platinum (Pt), Iron (Fe), Copper (Cu), Aluminum (Al), Zinc (Zn) or the like. Both the dimensions and geometry of a given type of nanoparticles may have an impact on the associated heating efficiency. In a preferred embodiment, the metal is gold. In another preferred embodiment, the preferred nanoparticles are gold nanorods. According to embodiments of the methods and systems of the present invention, the nanoparticles used in conjunction with UV light sources to perform the quantification should preferably possess minimal UV absorption properties.

The expression "photo-thermal properties", as used herein is meant to refer to the ability of a given type of nanoparticles to release heat as a result of an optical stimulation, i.e. the irradiation of these nanoparticles with a light beam having suitable optical characteristics. The photo-thermal properties may result from various chemical, geometrical or physical characteristics of the nanoparticles. In one embodiment, the photo-thermal properties include a localized plasmon resonance at a surface of the nanoparticles, resulting in a "plasmonic heating" effect. This effect is for example observed at the surface of gold nanoparticles, spherical or having another geometry. Plasmonic heating may also be observed on gold coated or decorated multiwalled carbon nanotubes. A localized surface plasmon originates from a strong interaction between gold or silver nanoparticles and excitation light having a wavelength which resonates with the surface plasmon. Under excitation by light at the resonance wavelength a polarized charge build up at the surface of the particle leads to an oscillating dipole around the particle that exhibits an enhanced absorption and scattering cross section. The resonant wavelength is determined by the size and geometry of the nanoparticles. The energy of the resonance of the oscillating dipole is dispersed through Ohmic heating losses to the surrounding medium, raising its temperature. The energy released can be used to heat a solution rapidly where each particle becomes a heating element.

In a preferred embodiment, the photo-thermal properties comprise a localized plasmon resonance at a surface of the chemically modified nanoparticles, and the activation light beam has a wavelength corresponding to the localized plasmon resonance.

In other embodiments, the photo-thermal properties may be any process by in which energy from light is absorbed by a nanoparticle, leading to an eventual decay resulting in conversion to heat energy to the surrounding media. Nanoparticles may be mono-dispersion in solution, in direct or indirect contact with reaction components or immobilized within a polymeric material or glass.

The contact between the reaction mixture and the nanoparticles may be direct or indirect. An activation light beam may be used to irradiate the nanoparticles, which therefore release heat according to their photo-thermal properties. The heat is transferred directly or indirectly to the reaction mixture. Therefore, the expression "contacting the reaction mixture with nanoparticles" is understood to refer to providing either direct contact, indirect contact or both at the same time.

In some embodiments, in particular where the nanoparticles are in direct contact with the reaction mixture, care should be taken so that the nanoparticles do not interfere with the DNA related process to be performed. For example, in PCR embodiments, the polymerase may bind to the surface of the nanoparticles, blocking positive active site by association with a negatively charge particle surface, and therefore inhibiting the polymerase from performing its function during the DNA amplification process. In accordance with some embodiments, therefore, the nanoparticles have a surface modification by a chemical compound such as polyethylene glycol (PEG) or any other chemical equivalent that prevents the inhibition of a positive active site of polymerase class enzymes.

One advantage of the surface modification described above is that the resulting nanoparticles can be used as generic heaters independently of the type of polymerase, size of the template or template type. Inhibition prevention will apply to any application, avoiding the additional complication of limiting the application of the method to specific polymerase types.

In various embodiments, the dimensions of the nanoparticles may be selected in view of optimizing the resulting heating efficiency. In various embodiments, other factors can be controlled to improve heating efficiency of the method. As predicted by the Beer-Lambert law, a higher rod concentration and shorter path-length will maximize the absorbance of the activation light beam.

In embodiments, the biological enzymatic reaction mixture is irradiated, during the annealing step, the elongation step, or both, with an ultraviolet (UV) light source, and the change in UV light transmission therefrom is measured to quantify amplification of the nucleic acid template. In embodiments, the irradiating is for a duration and at an intensity sufficient to measure a free nucleotide concentration therein, while avoiding inhibition of amplification of the nucleic acid molecule.

There is however a problem with using UV light to monitor PCR product. UVC (100 nm-280 nm) light is known to damage DNA and exposing DNA to both UVC and UVB (280 nm-315 nm) light may result in the formation of pyrimidine dimers. Pyrimidine dimers occur when there are two adjacent thymine base pair in a DNA sequence. Exposure to UV light causes the two thymine base pairs to link up through covalent bonding. Depending on the covalent bond, the two thymine base pair can form either a 6-4 product or a cyclobutate. The formation of these pyrimidine dimers causes a kink in the DNA sequence. Depending on the intensity of the UV radiation and exposure time, dsDNA might not form at all.

In embodiments, the monitoring is performed during annealing step, the elongation step, or during both. The duration is from about 10 ms to about 1000 ms, or the duration may be about 30 ms. In embodiments, the intensity may be from about 0.5 to about 1 mW.

System

Figure 7:
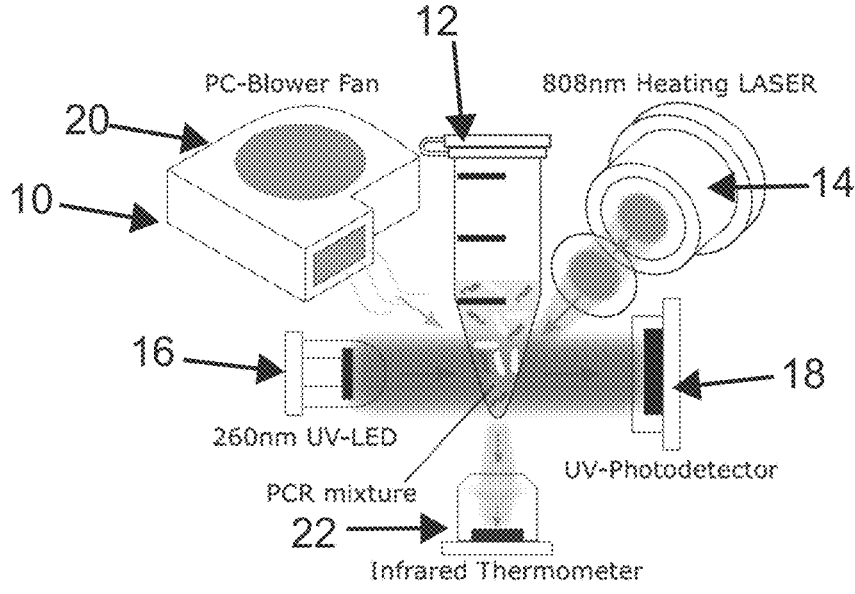
FIG. 7 illustrates a diagram of a system according to an embodiment of the present invention.

Now referring to FIG. 7. According to another embodiment, there is provided a system 10 for performing a polymerase chain reaction (PCR) or a loop-mediated isothermal amplification (LAMP) of a nucleic acid molecule and quantify amplification thereof.

The system 10 comprises at least one nucleic acid sample 12 containing a nucleic acid template, a polymerase enzyme, and chemically modified nanoparticles comprising nanorods of metal, metallic coated organic nanotubes, or a combination thereof, having photo-thermal properties, to promote the PCR or the LAMP.

The system also comprises a thermal cycler in thermal communication with the at least one nucleic acid sample. According to an embodiment, the thermal cycler may be any suitable means of regulating the temperature of the nucleic acid sample, such as a well-known PC-blower fan 20, which is inexpensive and efficient an increasing the cooling rate.

The system of the present invention will also comprise a continuous wave laser 14 configured to irradiate the at least one nucleic acid sample and provide excitation for a period of time to activate the photo-thermal properties of the chemically modified nanoparticles. The laser 14 may be part of a light generating assembly allowing a control of optical parameters of the activation light beam such as the wavelength, optical power, duty cycle in embodiments where the light beam is pulsed, spot size, etc. Embodiments of continuous wave laser include any suitable continuous wave lasers, and may include for examples compact lasers, which may be more suitable for use in device for use at the point of care (POC). Examples of compact laser are fibre-coupled laser and a vertical-cavity surface-emitting laser (VCSEL), or their combination. Various means of adjusting such parameters are well known in the art and need not be described here. By way of example, in the illustrated embodiment, the laser 14 generates an activation light beam having a wavelength of 808 nm resonant with a plasmon resonance of gold nanorods, and a coil-based shutter is provided in a path of the activation light beam 30 before it reaches the sample. The shutter may for example be used to periodically block the activation light beam to reduce the average light power reaching the sample. In other embodiments a different mechanism may be used to control the light power such as for example direct modulation of a laser 14 or LED light source (such as TTL modulation), use of a modulating device such as an intensity of phase modulator, etc. Of course, one skilled in the art will readily understand that a number of additional optical components may be provided in the system depending on particular design considerations, such as lenses, mirrors, filters, polarizers, amplifiers, and the like without departing from the scope of the present description.

The optical parameters of the activation light beam are preferably determined and controlled in view of the photo-thermal properties of the nanoparticles. By way of example, in one embodiment the necessary light power to achieve a desired temperature through release of heat from the nanoparticles can be calculated from theoretical considerations related to plasmonic heating. The heat released by a given nanoparticle can be evaluated using known equations.

Time of exposure can also be varied to control the raising of the temperature of the reaction mixture. As one skilled in the art will readily understand, the intensity of the activation light beam and the time of exposure are two parameters which can easily be controlled in conjunction to control the rate at which energy is transferred to the nanoparticles and, consequently, the temperature of the reaction mixture.

The wavelength of the activation light beam is another optical property which can be determined and controlled in view of the photo-thermal properties of the nanoparticles. As mentioned above, in the case of plasmonic heating, the release of heat by the nanoparticles results from their stimulation using light having a wavelength matching the localized plasmon resonance at the surface of the nanoparticles. Furthermore, in embodiments using light-induced plasmonic heating a wavelength selectable characteristic can be conferred upon the process of heating. Within the bandwidth of excitation, heating of a solution can be turned on and off readily, accentuated by greater dispersion of heat from the solution simply by the presence of nanoparticles within the reaction mixture that should, in effective combination with a cooling system, lead to rapid temperature transition, hence shorter PCR cycle times. Carbon nanotubes, in contrast, absorb light into energy levels pertaining to both the semi-conducting and, if metallic elements are present, energy levels pertaining to the presence of the metals. The broad absorbance of carbon nanotubes can be explained by many additional transitions possible from the ground state over the visible and into the near infra-red for the promotion of an electron. The wavelength of the absorbance pertains to the difference in energy between the ground state and the excited state. In any case, by choosing, and optionally varying, the wavelength of the excitation light beam to match a resonance or transition of the absorption spectrum of the nanoparticles, control of the heat released through the photo-thermal properties may be achieved and/or optimized.

The distance of the activation light beam provided by the continuous wave laser may also be modulated. In particular, this parameter may be of importance for compact continuous wave lasers, such as fibre-coupled laser and a vertical-cavity surface-emitting laser (VCSEL). In some embodiments, the activation light beam from the compact laser is provided from a distance of ≤5 mm from the biological enzymatic reaction mixture. In other embodiments, the activation light beam from the compact laser is provided from a distance of from about 1 mm to about 5 mm, or from about 2 to about 5 mm, or from about 3 to about 5 mm, or from about 4 to about 5 mm, or from about 1 mm to about 4 mm, or from about 2 to about 4 mm, or from about 3 to about 4 mm, or from about 1 mm to about 3 mm, or from about 2 to about 3 mm, or from about 1 mm to about 2 mm, or about ≤5, about ≤4, about ≤3, about ≤2, about ≤1 mm, or, about 5, about 4, about 3, about 2, about 1 mm from the biological enzymatic reaction mixture. In some embodiments, the activation light beam from the VCSEL is provided from a distance of ≤5 mm from the biological enzymatic reaction mixture. In other embodiments, the activation light beam from the VCSEL is provided from a distance of from about 1 mm to about 5 mm, or from about 2 to about 5 mm, or from about 3 to about 5 mm, or from about 4 to about 5 mm, or from about 1 mm to about 4 mm, or from about 2 to about 4 mm, or from about 3 to about 4 mm, or from about 1 mm to about 3 mm, or from about 2 to about 3 mm, or from about 1 mm to about 2 mm, or about $5, about ≤4, about ≤3, about ≤2, about ≤1 mm, or, about 5, about 4, about 3, about 2, about 1 mm from the biological enzymatic reaction mixture.

According to some embodiments, the system of the present invention may also comprise an ultraviolet (UV) light source 16 configured to irradiate the at least one nucleic acid sample, as well as corresponding photodetector 18 configured to measure the UV light absorbance from the at least one nucleic acid sample. According to an embodiment, the UV light source 16 is a UV light emitting diode (LED). The UV light source 16 may emit light having a wavelength of from about 175 nm to about 350 nm, or light having a wavelength of from about 240 nm to about 350 nm, or light having a wavelength of from about 260 nm to about 280 nm. According to an embodiment, the system may comprise a plurality of UV light source 16, configured to irradiate a plurality of nucleic acid sample. Along a similar line, the system may comprise a plurality of photodetector 18, configured to measure absorbance from a plurality of nucleic acid sample.

According to another embodiment, a UV light from the UV light source may be focused through an optical lense, a light pipe, or a combination thereof. In an embodiment, the UV light from the UV light source may be focused through a light pipe onto the photodetector 18. The optical lense and light pipe may contribute to provide a highly sensitive DNA detection system even for minimal optical intensity changes at the photodetector.

The system of the present invention may include any other component typical of DNA amplification, extraction or sterilization devices. For example, a fan controller will be included to allow a control of the activation of the thermal cycling fan. Overall control of the apparatus can be managed through any appropriate device or combination of devices. In the illustrated embodiment, by way of example only, a computer provides electrical control signals to the laser, the thermal cycler and UV light source through an appropriate electrical interface, for example an FPGA circuit board. Also, the computer can also act as a processor for analyzing the change in UV light transmission and quantify amplification of the nucleic acid template, according to the present invention.

According to another embodiment of the present invention, the system of the present invention may comprise a thermometer for monitoring bulk heating of the at least one nucleic acid sample. For example, the thermometer may be an infrared thermometer 22.

In accordance with another embodiment, there is disclosed systems for performing a polymerase chain reaction (PCR) or a loop-mediated isothermal amplification (LAMP) of a nucleic acid molecule, the system comprising:
  a) at least one nucleic acid sample containing
    a nucleic acid template,
    a polymerase enzyme, and
    chemically modified nanoparticles comprising nanorods of metal, metallic coated organic nanotubes, or a combination thereof, having photo-thermal properties, to promote the PCR or the LAMP;
  b) a thermal cycler in thermal communication with the at least one nucleic acid sample; and
  c) a compact continuous wave laser configured to irradiate the at least one nucleic acid sample and provide excitation for a period of time to activate the photo-thermal properties of the chemically modified nanoparticles.

The system may also further comprise:

d) an ultraviolet (UV) light source configured to irradiate the at least one nucleic acid sample;

e) a photodetector configured to measure the transmission changes in UV light absorbance from the at least one nucleic acid sample, and f) a processor for analyzing the change transmission changes in UV light transmission and quantify amplification of the nucleic acid template;

for quantifying amplification of the nucleic acid, wherein the chemically modified nanoparticles are nanorods of metal.

Real-Time Monitoring

In accordance with one aspect of the invention, the method may include an additional step of optically monitoring, in real time, the temperature change resulting from heating a reaction mixture according to embodiments of the invention and quantify the formation of dsDNA based on the measurement of the free nucleotide concentration in the reaction mixture.

In accordance with another aspect of the invention, the system may include a configuration for optically monitoring, in real time, the temperature change resulting from heating a reaction mixture according to embodiments of the invention and quantify the formation of dsDNA based on the measurement of the free nucleotide concentration in the reaction mixture.

According to an embodiment, the reaction mixture is irradiated with UV light during the annealing step, elongation step, or both, of each cycle of the PCR reaction or LAMP, for a duration and at an intensity sufficient to measure the free nucleotide concentration therein, while avoiding inhibition of amplification of the nucleic acid molecule. As indicated above, UV light exposure must be restricted to a minimal amount of time so as to prevent damaging the DNA and inhibit the PCR of LAMP reaction. Depending on the intensity of the UV radiation and exposure time, dsDNA might not form at all. Therefore, in embodiments, the monitoring is performed for a duration of from about 10 ms to about 10000 ms, or the duration may be about 30 ms, each cycle. Also, in embodiments, the intensity may be from about 0.5 to about 1 mW, each cycle. The monitoring may be only during the annealing step, only during the elongation step, during a period overlapping the annealing and elongation step, or during both the annealing and elongation steps. The collected readings may then be provided to the processor for analyzing the UV light transmission and provide quantification results of the nucleic acid template in real time. UV light diodes are significantly cheaper than visible light diodes, such as diodes used for monitoring of fluorescent dyes such as SYBR™ green.

Optical properties of nanoparticles can also provide a useful spectroscopic approach for real time monitoring of the reaction. A change in the temperature of the environment of the nanoparticles also affects the local dielectric constant, which leads in a drift of the optical properties of the nanoparticles. By using a probe light beam having a wavelength coordinated with a different absorption feature than the one used for heat release, this drift can be measured, therefore monitoring the corresponding temperature change, by interrogating the nanoparticle resonance with the probe light beam and monitoring a change in either the scattering or absorbance at a fixed probe wavelength.

In some other embodiments, probing nanoparticles having an absorption feature at a wavelength different from the wavelength used to activate the photo-thermal properties of the nanoparticles used for heating can be put in contact with the reaction mixture. The heating of the nanoparticles (e.g. the nanorods) having a localized plasmon resonance as explained above, releasing heat when irradiated with the activation light beam having a wavelength corresponding to that resonance, for example at about 532 nm or 808 nm when considering gold nanorods (both resonant frequencies can be changed by particle dimension and the dielectric constant of the medium or surface ligands around them). In an embodiment, the probed nanoparticle may be distinct from the nanoparticle used for heating of the reaction mixture. Probe nanoparticles, for example gold nanospheres, may be put in direct contact with the reaction mixture. In another embodiment, the gold nanoparticles (e.g. nanospheres) may be covalently attached to the primers and DNA template.

Covalent attachment of primers would result in a great local dielectric shift at the surface of the gold nanoparticles as amplicons would be confined in close proximity to the gold. The plasmonic field propagates approximately tens of nanometers from the surface and changes at the surface more greatly affect the plasmonic shift measured as a red shift of the plasmonic peak. The gold nanospheres used for sensing production of amplicons would have a resonance, blue shifted from the resonance of the nanorods used for heating purposes. The probe nanoparticles are irradiated with a monitoring light beam having a wavelength within the resonance of the gold nanospheres. Return light resulting from the interaction of the monitoring light beam with the monitoring nanoparticles is detected and analyzed. The intensity of the return light varies according to the degree of absorption of the monitoring light beam by the gold nanospheres. As the temperature varies, the resonance of the monitoring nanoparticles shifts, and the wavelength of the monitoring light beam falls in and out of resonance, changing the degree at which the monitoring light beam is absorbed.

In one example, gold probe nanoparticles are covalently linked to the primers through a thiol linkage added to the 5' end of the primer and linked to the gold through the sulphur atom. As PCR proceeds through annealing, elongation and denaturation, the dielectric constant around the nanoparticle will change dynamically, first with the binding of single strand DNA to primers, then with elongation of the single strand to double strand and finally again with removal of double stranded copy from particle surface. The stage of the reaction could be monitored similarly to that of SYBR™ green fluorescence during real time PCR. Using a separate plasmonic resonance for the probe and heating nanoparticle species, the heating nanoparticles will not interfere with measurement at the probe wavelength relative to the resonance of the probe nanoparticles. In some embodiments, the probe nanoparticles may have a spherical geometry and be assess by illumination with white light and measuring the absorbance using a CCD with a bandpass filter centered around the resonance peak. The heating nanoparticle species may be gold nanorods as nanorods have greater extinction coefficients than spherical particles and will produce more heating power per unit of laser power incident upon the nanoparticles.

The wavelength used to initiate plasmon resonance is dependent upon the geometry of the particle. For example, a 532 nm may not represent an optimum combination of laser wavelength and particle for some applications and can be modified depending on the particles and conditions used. The high cost of lasers in this spectral range would impact upon the uptake of this method, and light source costs can be significantly reduced by using a less expensive laser system or a LED and choosing and designing the nanoparticles accordingly. Heat transfer can be improved by using a particle with a large absorption cross-section and hence great extinction co-efficient. One combination consists of a 1 W laser diode at 808 nm and gold nanorods with an absorptivity of $5.96 \times 10^{12}$ $M^{-1}$ $cm^{-1}$ at the same wavelength. This takes advantage of a significant cost reduction and increase in efficiency of heat generation by nanoparticles and offers the potential for multiple nanoparticle systems that could be easily multiplexed. In such a system, heating could be accomplished by a class of nanoparticles with a superior absorption cross-section and another class(es) of nanoparticles modified using primers could be used as the probe for the reaction, demonstrating binding of new ampli-con fragments upon the particle surface by changing the resonant absorbance and spectral position.

In other variants, the same nanoparticles used to release heat may be used for optical monitoring as well. For example, in the case of nanorods, the elongated geometry of the nanoparticles results in two distinct surface plasmon resonances, respectively aligned with the longitudinal and transversal axes of the nanorod. These two resonances interact with light at very distinct wavelengths—for example, the longitudinal resonance of gold nanorods absorbs light around 808 nm, whereas the transverse resonance absorbs light around 560 nm, and can be used as the monitoring resonance.

The present invention will be more readily understood by referring to the following examples which are given to illustrate the invention rather than to limit its scope.

EXAMPLE 1

Nanoparticle Inhibition of PCR

One of the drawbacks of PCR is that there is a wide range of chemical and biological substances that prevent PCR from occurring by interacting with one or more PCR components. An example of a PCR inhibitor is SYBR™ green fluorescent dye, as the intercalation process itself inhibits the PCR. However, SYBR™ green is still used in quantitative PCR because the inhibition concentration is higher than the concentration of SYBR™ green required for the fluorescent signal to be measurable.

Figure 2:
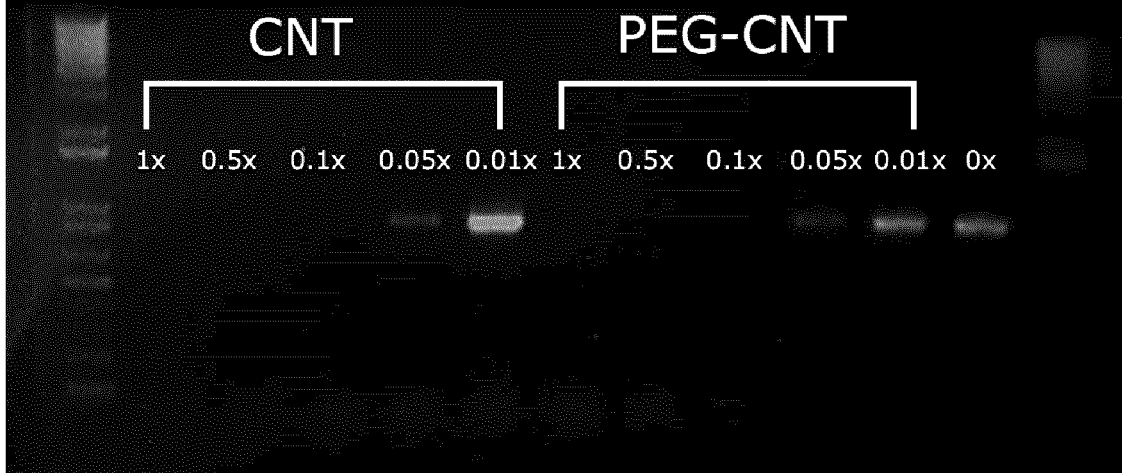
FIG. 2 illustrates gel electrophoresis for PCR reactions performed in the presence of MWCNT and PEGylated MWCNT (1× represents 1 g/L, 0.5× represents 0.5 g/L and so on).

PEGylation is the process of coating the nanoparticles with polyethylene glycol (structure shown in FIG. 1). Experimentally, for some nanoparticles this coating helps prevent inhibition. In PEG 5000, which is used in the present invention, the n in FIG. 1 means that the unit is repeated 5000 times. In these experiments a typical PCR solution replicating gonorrhea DNA was prepared, using both multi wall carbon nanotubes (MWCNT) and PEGylated MWCNT with different concentrations. The MWCNT have an average length of 1 μm and an average radius of 30 nm. The solution was then put through thermal cycling with conventional contact PCR. Inspecting the gel electrophoresis results in FIG. 2, it can be seen that PEGylation does not increase the inhibition concentration of 0.05 g/L of MWCNT.

Figure 3:
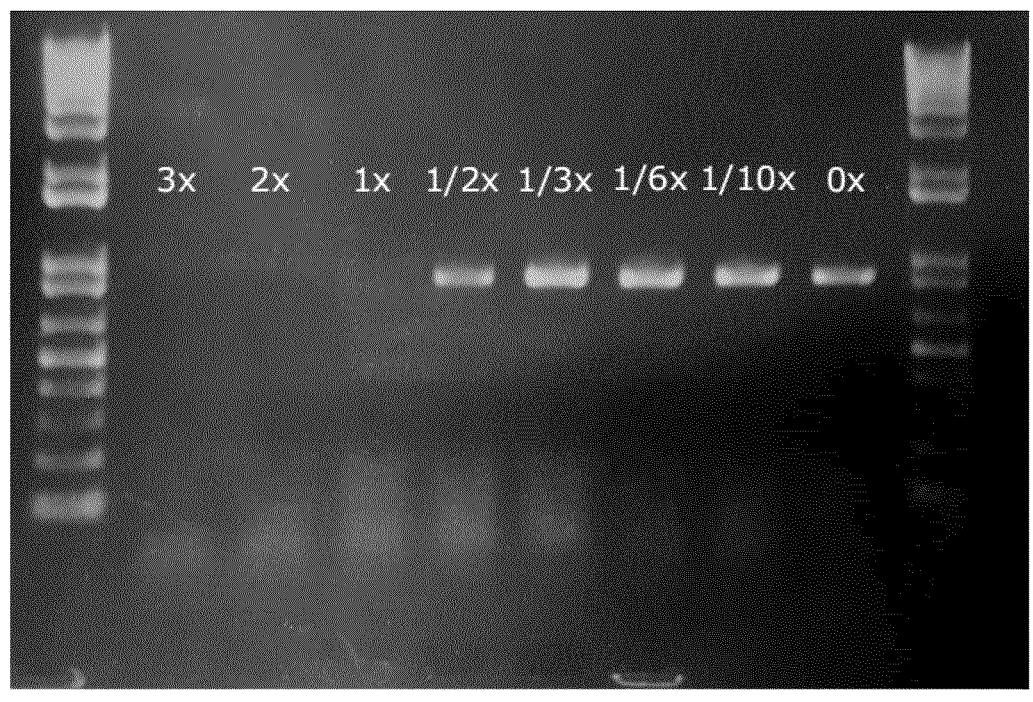
FIG. 3 illustrates gel electrophoresis for PCR reactions performed in the presence of Gold Nanorods (1× represents 1 nM, ½× represents 0.5 nM and so on).

The same experiment was done for gold nanorods purchased from Nanopartz™ with a radius of 10 nm and an aspect ratio of 4:1. The results for the inhibition concentration are shown in FIG. 3. It is seen that the inhibition concentration for uncoated gold nanorods is around 0.5 nM.

Figure 4:
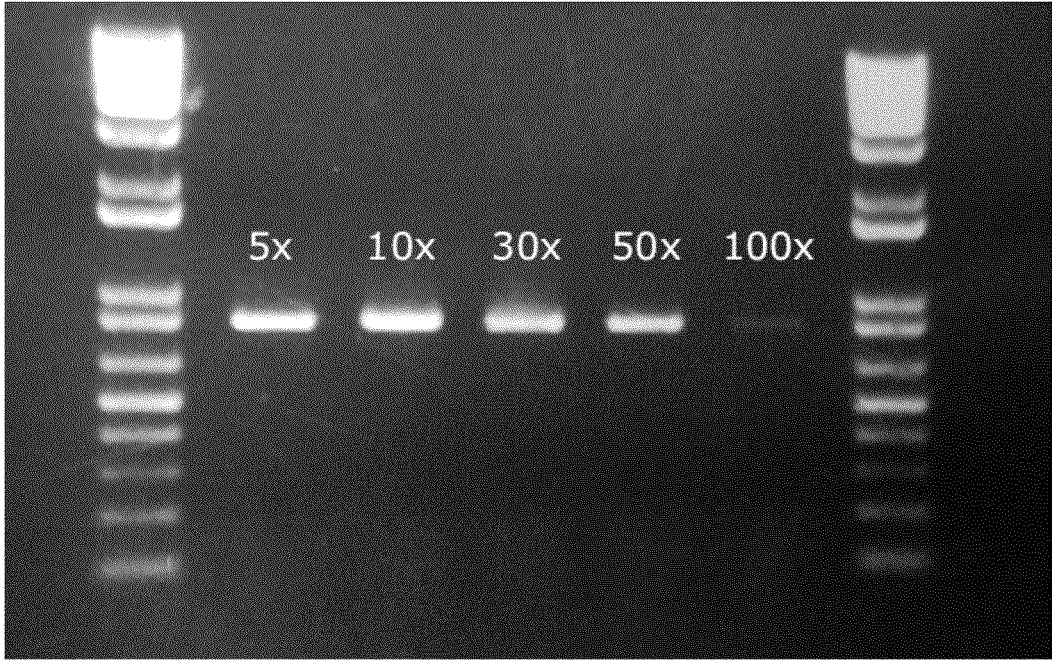
FIG. 4 illustrates gel electrophoresis for PCR reactions performed in the presence of PEGylated Gold Nanorods (5× represents 5 nM, 10× represents 10 nM and so on).
Figure 5:
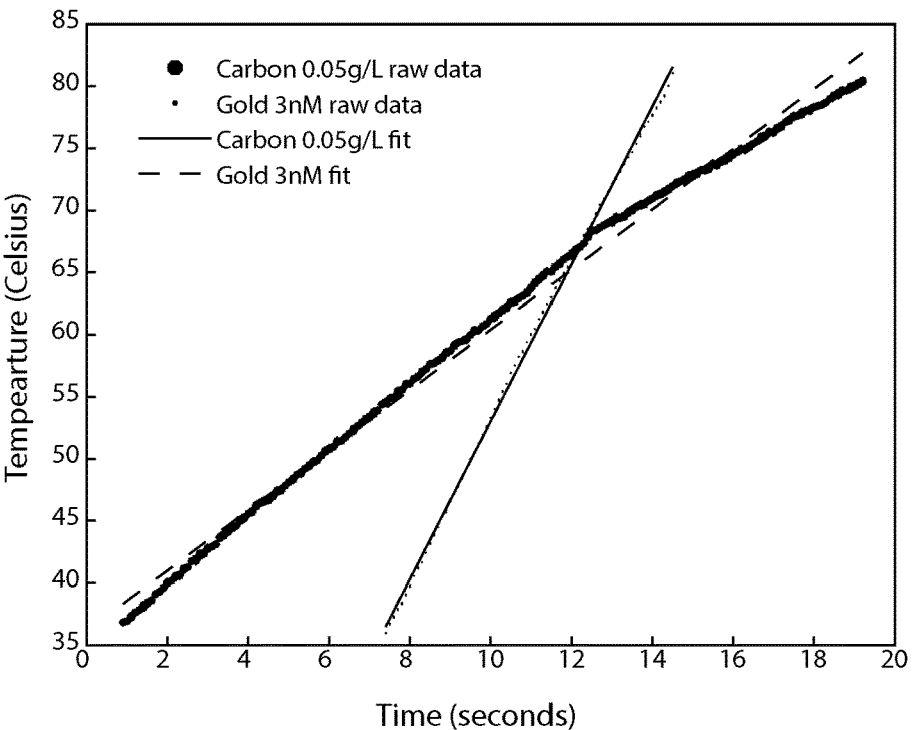
FIG. 5 illustrates heating curve of gold nanorods and MWCNT.

The results for PEGylated gold nanorods are shown in FIG. 4. It is seen that for gold nanorods, the process of PEGylation with PEG 5000 drastically increased the inhibition concentration, to approximately 100 nM. The exact interaction mechanism of these nanoparticles which inhibit PCR is not well understood, or which PCR component(s) interact with the nanoparticles to prevent inhibition. A summary of the inhibition concentration of these nanoparticles is shown in table 1.

TABLE 1

Summary of inhibition concentrations for CNT and gold nanorods.

| | CNT | PEGylated CNT | AuNR | PEGylated AuNR |
|---|---|---|---|---|
| Inhibition Concentration | 0.05 g/L | 0.0 5g/L | 0.5 nM | 100 nM |

Assuming negligible scattering from nanoparticles, eq. (1) gives us the ratio of heating rate to be:

$$\frac{R_1}{R_2} = \frac{1 - 10^{A_1 c_1 l}}{1 - 10^{A_2 c_2 l}}. \qquad \text{Eq. 1}$$

Where $R_1$, $A_1$, $c_1$ are the heating rate, absorbance per unit length concentration, and concentration of gold nanorods. $R_2$, $A_2$, $c_2$ are the heating rate, absorbance per unit length concentration, and concentration of MWCNT. Using eq. (1) $A_2$ is approximated to be 1.463

$$\frac{R_1}{R_2} = \frac{1 - 10^{A_1 c_1 l}}{1 - 10^{A_2 c_2 l}}. \qquad \text{Eq. 1}$$

We can thus find the maximum absorbance per unit length for both the MWCNT and gold nanorods before PCR inhibition.

$$\text{Maximum } OD \text{ per unit length for } MWCNT = 0.0446 \frac{1}{mm}$$

$$\text{Maximum } OD \text{ per unit length for Gold Nanorods} = 3.05 \frac{1}{mm}$$

It can be concluded that PEGylaged nanorods can have an absorbance per unit length 68 times higher than both PEGylated and non-PEGylated MWCNT.

EXAMPLE 2

System Justifications

A system which performs PCR with four main key characteristics is required: energy efficient, fast, compact, no down-time.

2.1: Heat Generation Mechanism

Traditional contact heating elements are simple and cheap but at the same time slow and inefficient. The heating element in addition to the PCR tube and reagent would have to be heated. Because heat is transferred through convection and conduction, heat loss due to coupling is the other drawback of contact heating. For non-contact heating, we require a source that is spatially coherent enough to couple effectively into with PCR reagents: this requirement can be fulfilled with a laser. To generate heat with a laser, either a laser in the mid-infrared range could be used or nanoparticles could be added to the PCR mixture and a laser close to the visible spectrum used. The latter is used in the form of a laser at 808 nm, and gold nanorods, as they are widely available. Using nanoparticles also provides the option of tuning the absorption.

Figure 6:
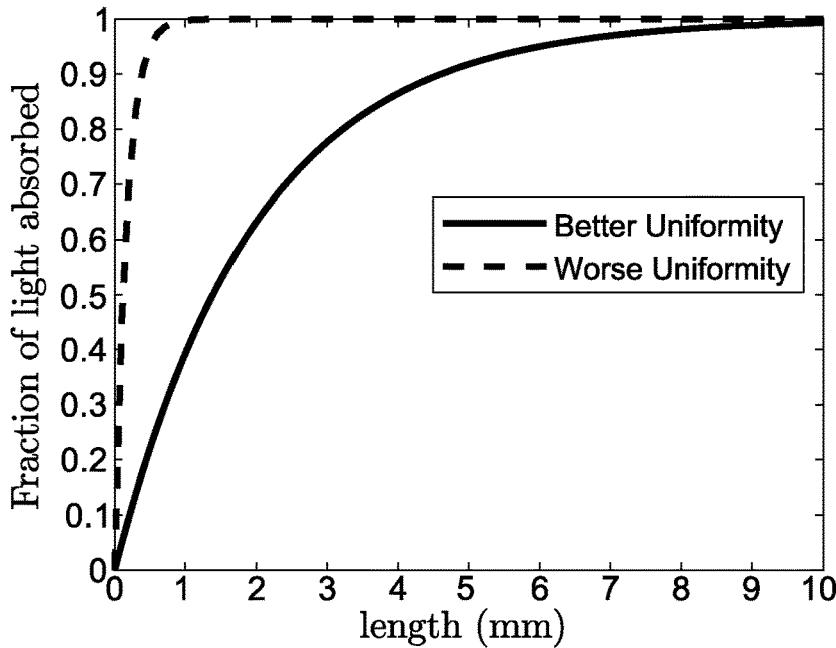
FIG. 6 illustrates the fraction of light absorbed as a function of length.

The amount of power absorbed from the laser is typically $$P_{abs} = P_{laser} \frac{\sigma_{abs}}{\sigma_{abs} + \sigma_{scattering}} \left(1 - e^{-(\sigma_{abs} - \sigma_{scattering})Nl}\right). \qquad \text{Eq. 2}$$

where N is the particle concentration, and/the optical path length which would also be the inner diameter of our tube. For a fixed path length, the concentration should be high enough such that most of the power is absorbed. However, if the concentration becomes much larger relative to the path length, non-uniform heat distribution would be obtained, which would be detrimental for PCR. In FIG. 6, for a fixed path length of 10 mm, approximately 100 percent of the light absorbed for both the lower concentration blue curve (absorption per unit length of 0.5 mm$^{-1}$) and the higher concentration, orange curve (absorption per unit length of 6 mm$^{-1}$). However almost all the light is absorbed in the $\frac{1}{10}$ the length of the tube, giving terrible heat distribution.

Using nanoparticles allows to always find the optimal concentration for a certain optical path length. This would not be possible to do relying on water absorption in the infrared or microwave spectrum, as the absorption per unit length is fixed and cannot be tuned.

From eq. A and eq. B below, the mass and in turn the volume is to first order approximation inversely proportional to the heating rate. It would be to one's advantage to use the smallest volume possible. However, pipetting becomes a challenge as volumes get smaller. A volume of 20 µL was selected as the optimal volume before any challenge in pipetting occurs. This corresponds to about 20 mg of water. The PCR mixture is contained in a standard Eppendorf polypropylene PCR tube.

$$T(t) = T_o + \frac{P_{in}(1 - e^{-\mu cl})}{hS}\left(1 - \exp\left(-\frac{hs}{m_w C_w}t\right)\right) \qquad \text{Eq. A}$$

$$T(t) = T_o + (T(0) - T_o)\exp\left(-\frac{hs}{m_w C_w}t\right) \qquad \text{Eq. B}$$

2.2: Thermometer

Small contact thermometers such as thermocouples or thermistors will have the highest temperature reading accuracy as they are physically in contact with the solution. This however would mean that the PCR machines will have significant downtime, as after each PCR run, the thermometer would have to be cleaned thoroughly to prevent cross contamination. This fact alone dictates the use of an infrared thermometer. The trade-off with infrared thermometers is that although thermal coupling between a liquid and a solid is quite high, the measured temperature will always be that of the tube but not of the solution itself. However, this may not be a significant problem, as the margin of error for PCR temperature is already rather large. The infrared thermometer may be calibrated with a heating block and thermocouple.

2.3: Cooling

Although the system of the present invention can be cooled passively as all the temperature steps for PCR are higher than typical room temperatures, a PC-blower fan is cheap, simple and drastically increases the cooling rate.

2.4: Real-Time Monitoring

As a diagnostic device, real-time monitoring of DNA product is the other key aspect of the system of the present invention. Although nucleic acid stain such as SYBR™ green and PICO™ green can be used, these nucleic acid stain suffers from photobleaching, wherein they permanently lose their ability to emit light even when excited at the correct wavelength. This is further amplified in laser-based system such as this one as they are constantly being exposed to a heating laser.

Figure 8:
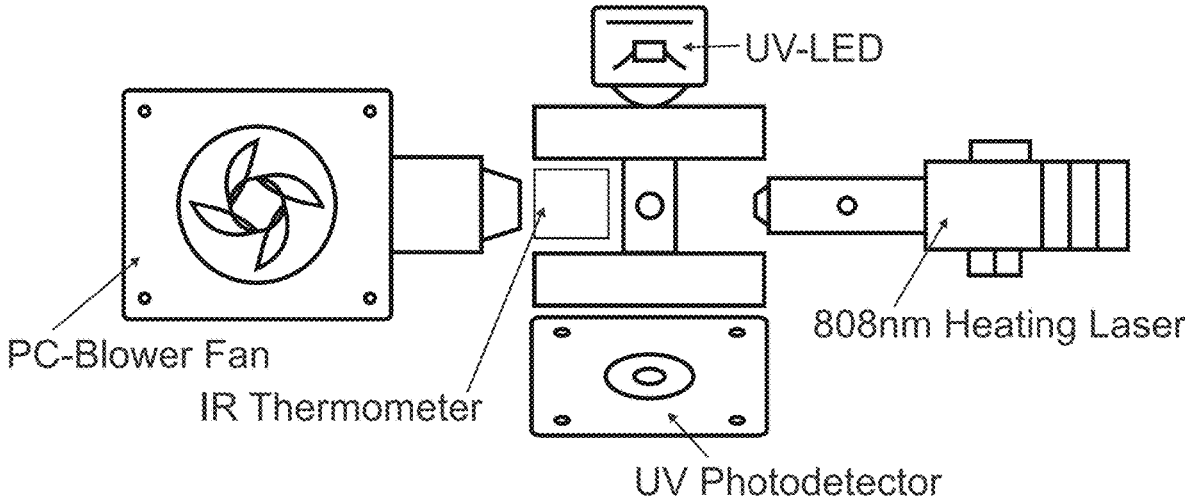
FIG. 8 illustrates a system according to an embodiment of the present invention.

For the reasons listed above it is believed that the simplest and most effective method is to measure the transmission of a 260 nm, 1 mW UV LED which may be performed effectively. The reason lies in the traditional contact heating mechanism: all contact heating requires a heat spreader. For the heat spreader to maximize its efficiency it would have to wrap over the entire tube. This however leaves only the top facet left to be accessed. One would need two facets in the same dimension to measure UV transmission. This is the other advantage of direct non-contact heating. The diagram of a system according to the present invention is shown in FIG. 7 and the picture of such a system is shown in FIG. 8.

TABLE 2

Summary of exemplary system's components.

|  | Manufacturer | Model Number |
|---|---|---|
| Heating Laser | Laserglow | D8050BXSX |
| Infrared Thermometer | Optris | CS LT |
| Cooling Fan | Sanyo Denki | 9BMB12P2K01 |
| UV LED | Thorlabs | LED260.J |
| UV Photodetector | Thorlabs | PDA25K |

2.5: Control System

Figure 9:
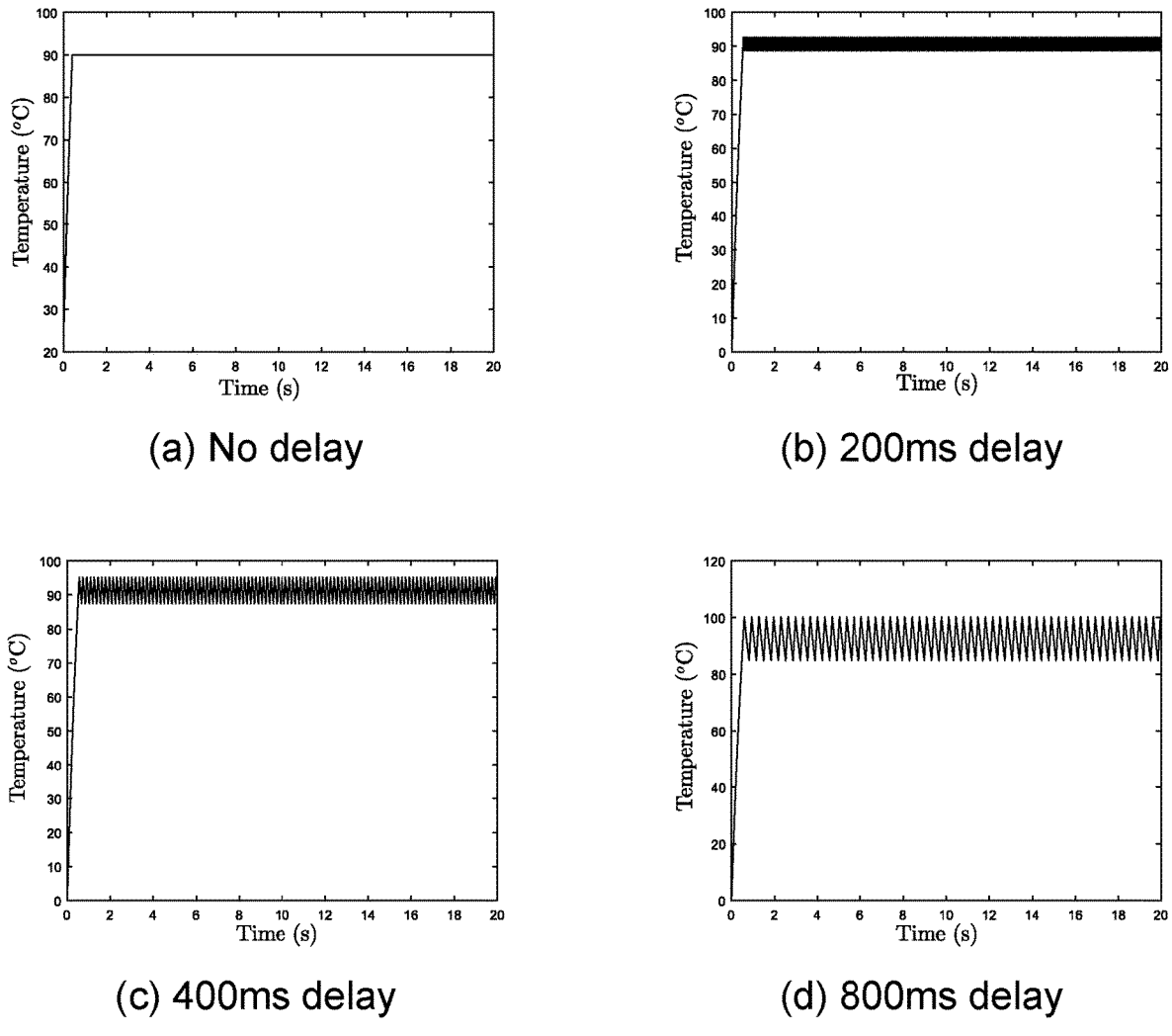
FIG. 9 illustrates the effect of delay on on-off control systems, plotted for temperature as a function of time.

As being able to reach different temperature quickly for different steps of a PCR cycle is the most important factor, on-off control should be implemented. The disadvantage comes in the form of oscillation in steady-state. The larger the delay in the response time of the system, the larger this oscillation will be. This effect is shown in FIG. 9, by applying finite time difference approximation to eq. C in conjunction with the on-off control algorithm.

$$m_w C_w \frac{dT}{dt} = P_{in}(1 - e^{-\mu cl}) - hS(T - T_o) \qquad \text{Eq. C}$$

As mentioned before, proportional control is often introduced to dampen the oscillatory behaviour of the system at equilibrium. The heating system employed in the present invention cannot truly have proportional control, as the cooling rate is always fixed and cannot be controlled, additionally the output power is clamped at the maximum power of the laser. The control parameter that is fed into the laser takes the form:

$$C = \begin{cases} \frac{c(t)}{K} & (1 \text{ for } C > 1) \text{ for } c > 0 \\ 0 & \text{for } c < 0. \end{cases}$$

Figure 10:
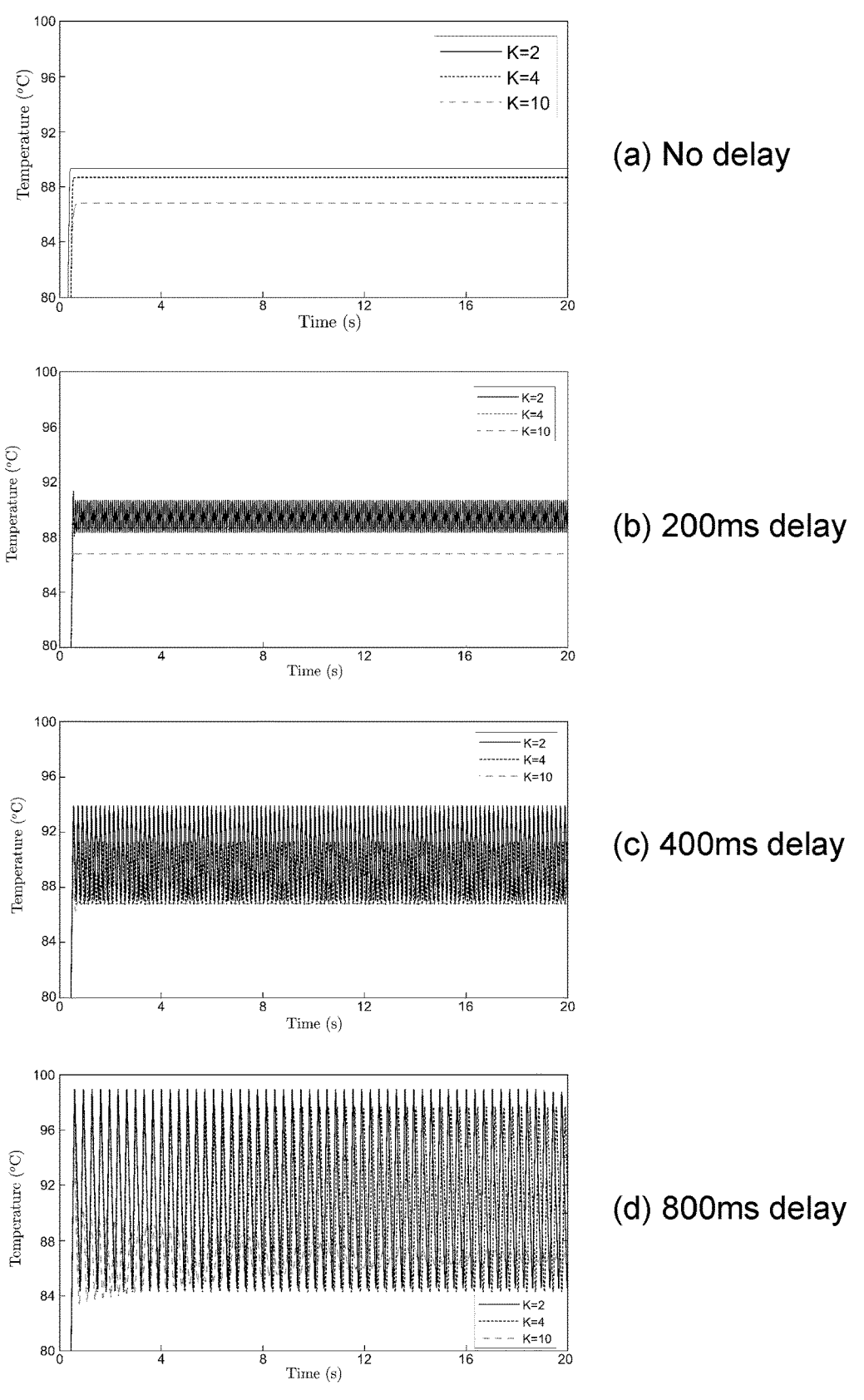
FIG. 10 illustrates the effect of delay on proportional control systems, plotted for temperature as a function of time.

In FIG. 10, we see that although large K parameters can dampen out the oscillation even when the delay in the system is large, this causes the equilibrium temperature to be lower than the actual target temperature of 90° C. (see FIG. 10). Experimentally it was found that the delay is small enough to keep the oscillation of on-off control within 1° C. of the target temperature. Due to the downside associated with proportional control, it is believed that the simple on-off control is most effective for fast PCR.

EXAMPLE 3

Heating Data

Figure 11:
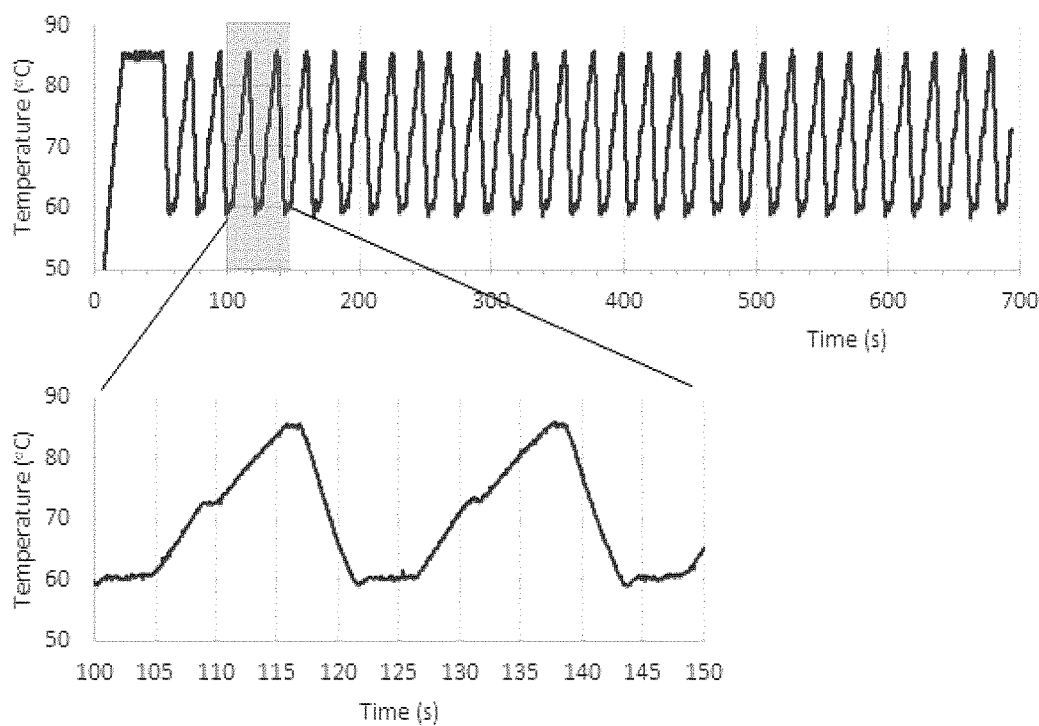
FIG. 11 illustrates a system heating curve for 35 PCR cycles, according to an embodiment of the present invention.

The 200 µL PCR tubes filled up to 20 µL have an average inner diameter of about 3 mm, taking this as the optical path length and using eq. D, $$Q_{in}=(P_{in}-P_{out})\eta=P_{in}(1-e^{-\mu el})\eta \qquad \text{Eq. D}$$

it is predicted that about 82% of the light will be absorbed. The heating curve of the PCR cycle is shown in FIG. 11. The temperature was held at each stage for 5 seconds. The basic temperature statistics at each holding stage are summarized in table 3.

TABLE 3

Temperature statistics at each PCR stage.

|  | Denaturation | Annealing | Elongation |
| --- | --- | --- | --- |
| Target Temperature | 90.5° C. | 61.5° C. | 71.5° C. |
| Average Temperature | 90.7° C. | 61.8° C. | 71.6° C. |
| Temperature Fluctuation | ±0.34° C. | ±0.55° C. | ±0.28° C. |

Because the input power is very large, eq. A can be linearly approximated to, $$T(t) = T_o + \frac{P_{in}\left(1 - e^{-\mu cl}\right)}{m_w c_w}t. \qquad \text{Eq. 3}$$

Figure 12:
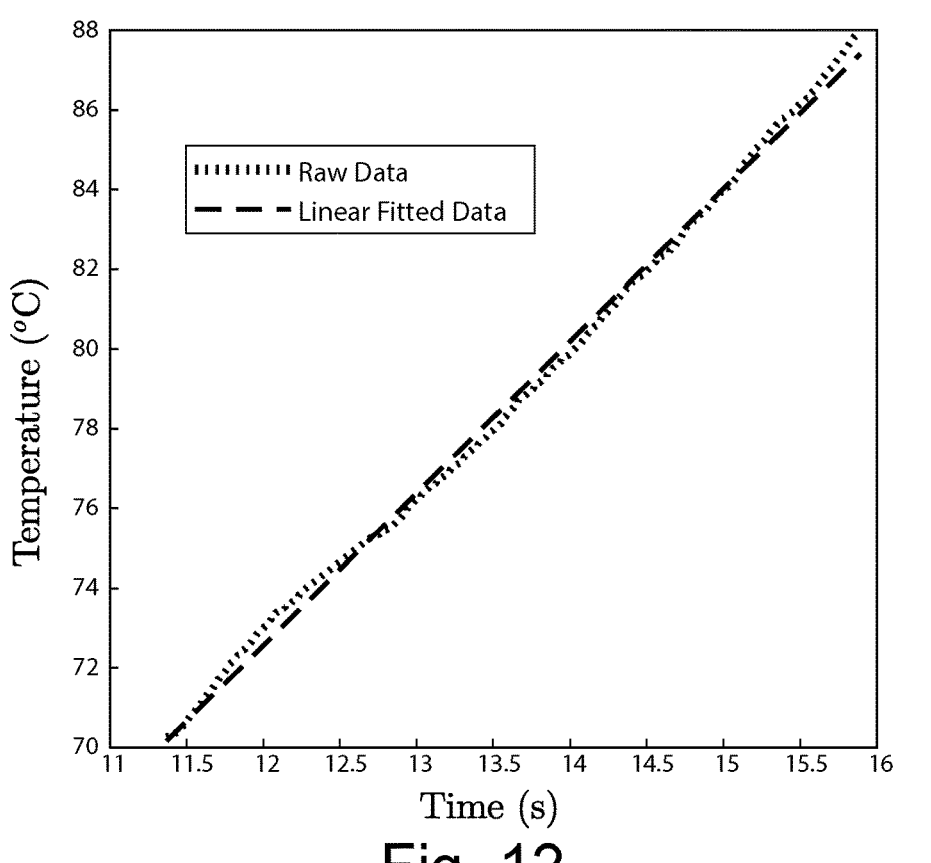
FIG. 12 illustrates the validity of Linear Approximation.

It can be clearly seen from FIG. 11 and FIG. 12 that even at the highest temperature range (72° C. to 91° C.), our linear approximation is still valid. With 2 W of power coming from the laser heating 25 mg, eq. (3) predicts that the heating rate should be 19.09° C./s, which is much higher than the experimental heating rate of 6.12° C./s. This is most likely due to the mass of the polypropylene PCR tube not being included in the calculations, as it is the temperature of the tube that is being measured. If the mass of polypropylene is taken into account, $m_w c_w$ would have to change to $$m_{eff}c_w=m_w c_w+m_{pp}c_{pp}. \qquad \text{Eq. 4}$$

Where $m_p p$, $c_{pp}$ are the mass of polypropylene and heat capacity of polypropylene respectively. Hence, with the polypropylene tube the effective water mass becomes $m_{eff}=78$ mg.

EXAMPLE 4

PCR Optimization
4.1: PCR Temperatures

Figure 13:
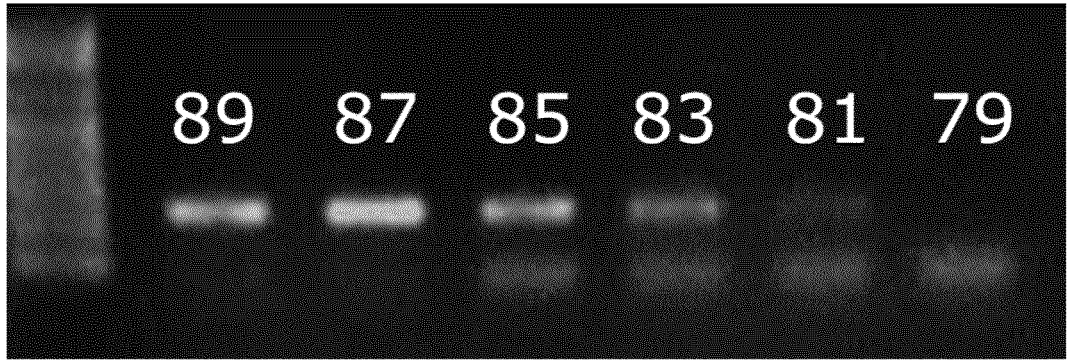
FIG. 13 illustrates a gel electrophoresis of PCR reactions performed with varying denaturing temperatures from 79° C. to 90° C.
Figure 14:
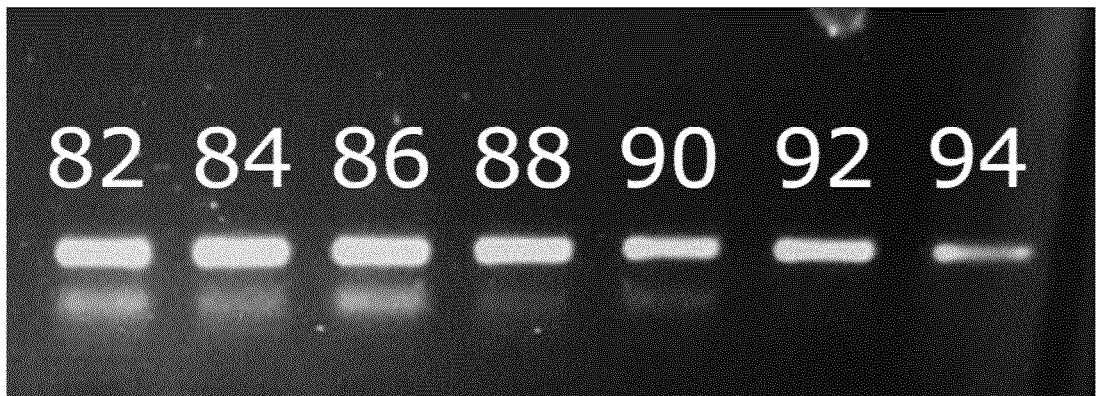
FIG. 14 illustrates a gel electrophoresis of PCR reactions performed with varying denaturing temperatures from 82° C. to 94° C.

The temperature range and the efficiency in this range for temperatures at each stage are next investigated. FIG. 13 and FIG. 14 show the electrophoresis gel image with varying denaturing temperatures for plasmonic PCR. The temperature was held for 5 seconds at each PCR stage of denaturing at varying temperatures, annealing at 55° C., and elongating at 72° C. for 30 cycles, with as starting DNA concentration of 104 *Chlamydia Trachomatis* (CT) DNA copies per 20 µl. It can be seen that the PCR is most efficient at 87° C. for the denaturing stage. This is because not enough template DNAs denature at low denaturing temperatures, while denaturing temperatures too high will permanently damage the polymerase.

Figure 15:
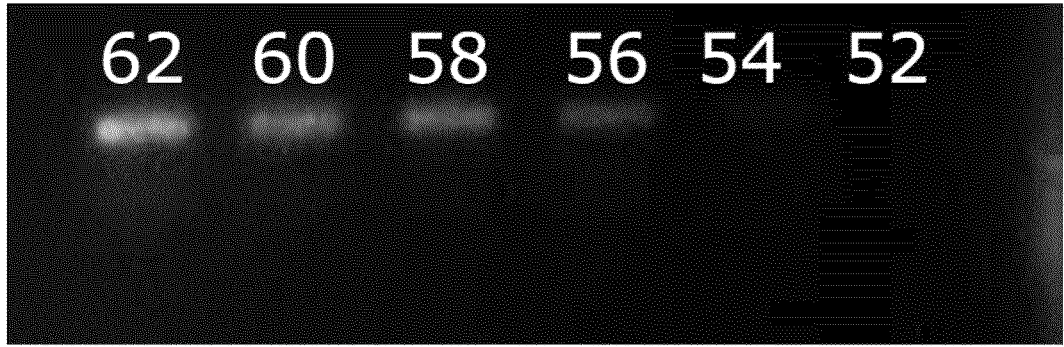
FIG. 15A illustrates a gel electrophoresis of PCR reactions performed with varying denaturing temperatures from 52° C. to 62° C.
FIG. 15B illustrates a gel electrophoresis of PCR reactions performed with varying denaturing temperatures from 60° C. to 66° C.
Figure 15:
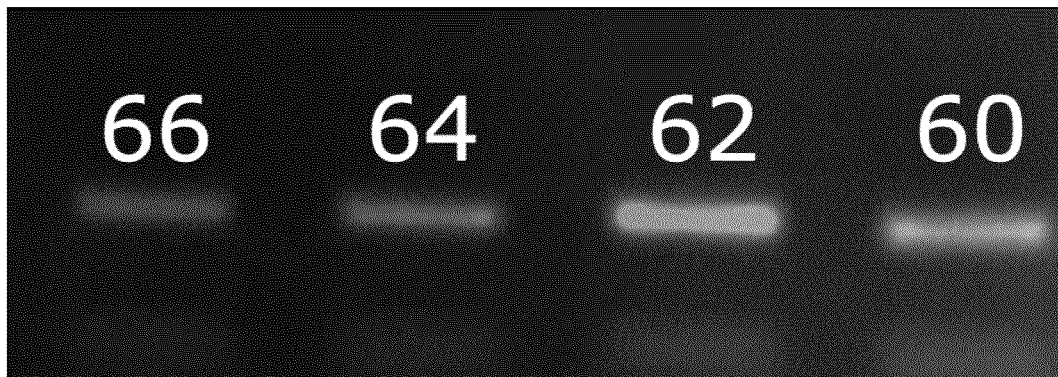
Figure 16:
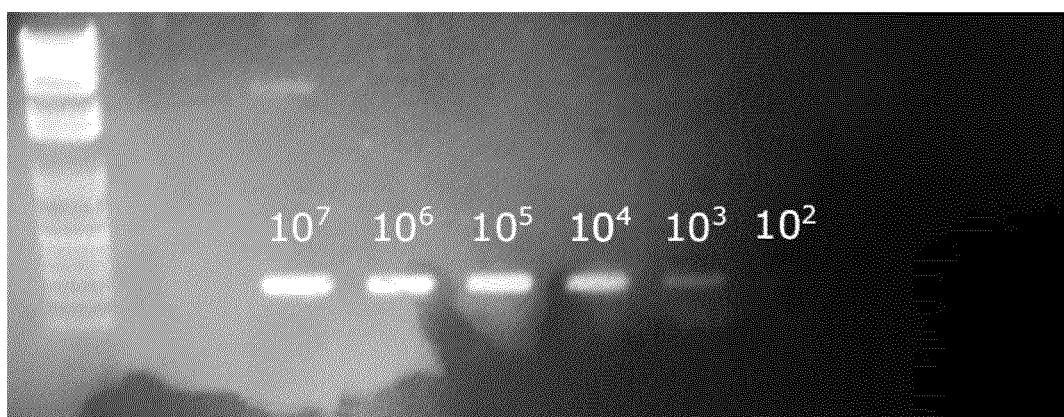
FIG. 16 illustrates a gel electrophoresis with varying starting DNA concentrations, each number represents the copies of DNA per 20 μl i.e. $10^n$ represents $10^n$ DNA copies per 20 μL.

The annealing temperature was then varied while keeping the denaturing stage at 87° C. and elongating stage at 72° C. for 30 cycles. All stages were held for 5 seconds and the resulting electrophoresis gel image is shown in FIGS. 15A-B.

It can be observed that the optimal annealing temperature is at 62° C. Lower temperature leads to nonspecific binding, while higher temperature will prevent efficient binding of the primers.

4.2: Limit of Detection

What is the minimum starting DNA concentration which will allow one to confirm PCR has occurred? Of course, the answer to this question would depend on what the exact detection method is. The detection limit for the semi-quantitative method of ethidium bromide gel electrophoresis is for explored. The starting DNA concentration is varied while keeping the optimal PCR temperatures from section 4.1, holding for 5 seconds at each stage for 30 cycles. It can be seen that the limit of detection for ethidium bromide is at 103 DNA copies per 20 µL.

4.3: Hold Time Limit

Figure 17:
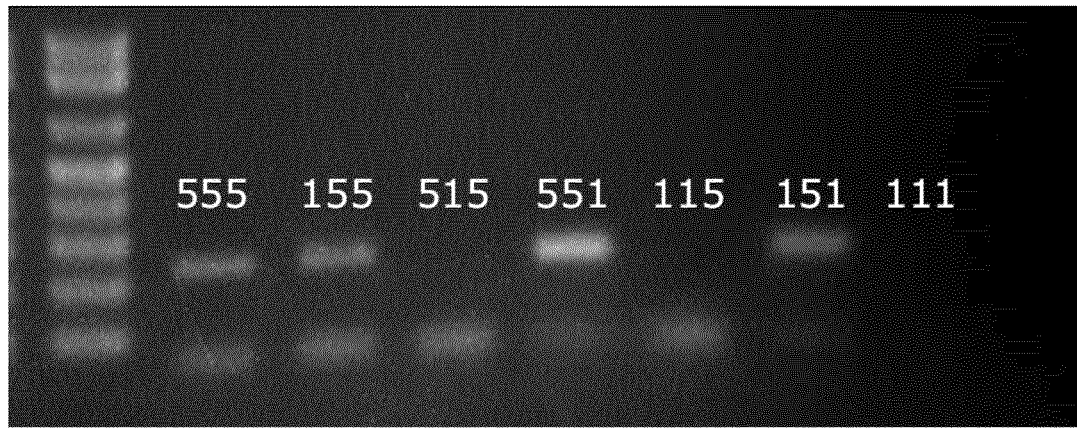
FIG. 17 illustrates a gel electrophoresis with varying hold time at optimal PCR temperatures. n1n2n3 represent holding for n1 seconds at denaturing, n2 seconds at annealing and n3 seconds at elongation (e.g. 555 means 5 seconds for denaturating, 5 seconds for annealing and 5 seconds for elongation).

As having a fast reaction is an important criterion, it was explored if there are any other parameters that can be changed to have a PCR product in a shorter time. This was investigated by changing the hold time at each PCR stage and the results are shown in FIG. 17. It can be seen that the hold time can be reduced to 1 second for both elongating and denaturing stage. However, no visible PCR product can be observed when the annealing temperature is reduced to 1 second.

Figure 18:
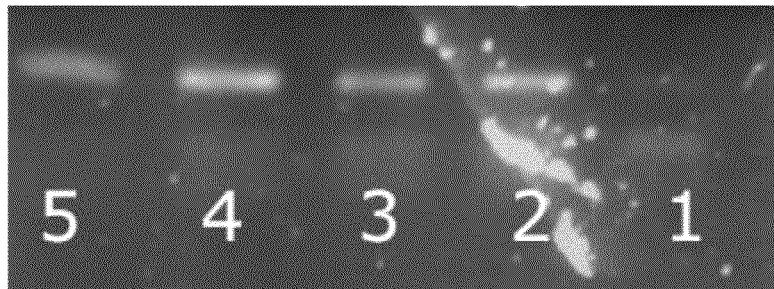
FIG. 18A illustrates a gel electrophoresis of PCR reactions performed with annealing time with annealing temperatures at 60° C.
FIG. 18B illustrates a gel electrophoresis of PCR reactions performed with annealing time with annealing temperatures at 62° C.
FIG. 18C illustrates a gel electrophoresis of PCR reactions performed with annealing time with annealing temperatures at 64° C.
Figure 18:
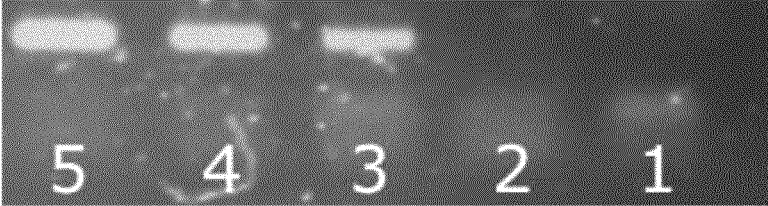
Figure 18:
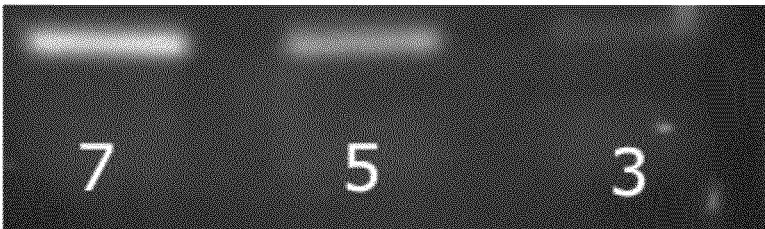

The annealing temperature was varied from 60° C. to 62° C. and annealing time. In the gel electrophoresis results shown in FIG. 18, it can be seen that the hold time could be further reduced by having a lower annealing temperature. At 60° C. the hold time can be reduced to 2 seconds. Although the band is very faint, PCR technically did occur even with a hold time of 1 second when the annealing temperature is at 60° C. Increasing the annealing temperature to 64° C. requires a longer hold time, as the band is already very faint at a hold time of 3 seconds. The results are in strong agreement with the experimental and theoretical data from Mamedov. If one wishes for maximum PCR efficiency, the hold time would have to be longer for higher annealing temperatures.

The total PCR hold time follows the simple formula:

$$t_{TotalPCR}=\text{cycles}\times(t_{hold_{anneal}}+t_{hold_{elongate}}+t_{hold_{denature}}+ \\ (H_R+C_R)(T_{denature}-T_{annealing})). \qquad \text{Eq. 5}$$

where $t_{hold\ anneal}$, $t_{hold\ elongate}$ and $t_{hold\ denature}$ are the annealing hold time, elongation hold time and denaturing hold time, respectively. $H_R$, $C_R$, $T_{denature}$ and $T_{annealing}$ are the average cooling rate, average heating rate, denaturing temperature, and annealing temperature. To optimize the PCR time and PCR efficiency for the system of the present invention, one would want the annealing temperature to be around 62° C. with a hold time of 3-4 seconds.

4.4: Beam Size

Figures 19, 20, 21, 22:
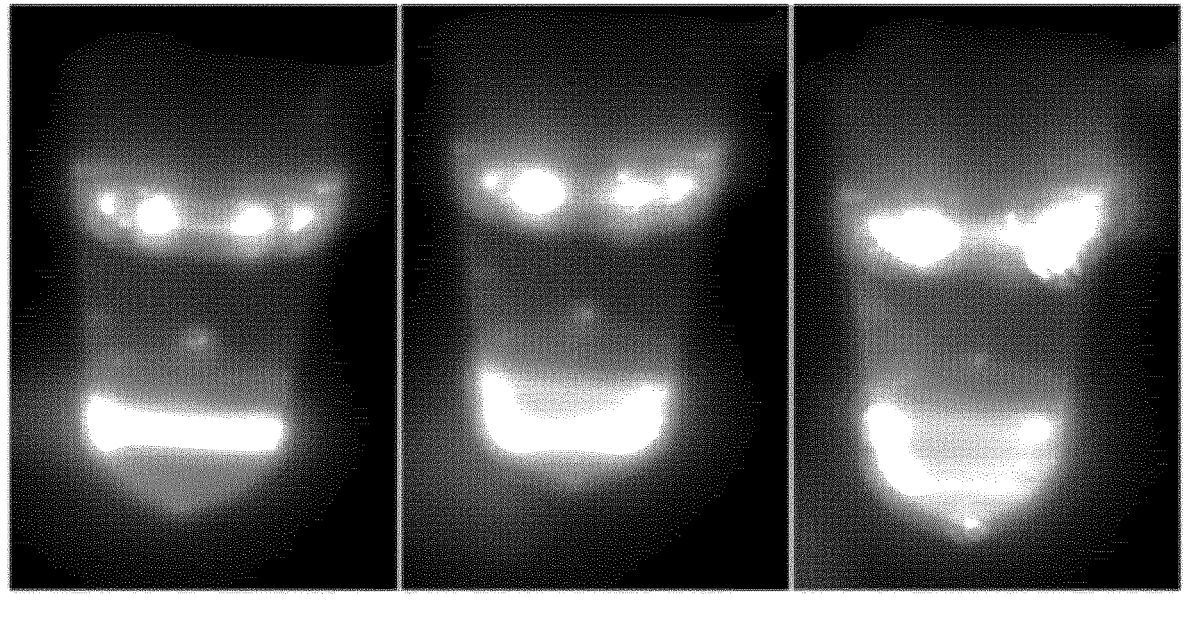
FIG. 19 illustrates a gel electrophoresis of a PCR reaction performed with a small beam size.
FIG. 20 illustrates a gel electrophoresis of a PCR reaction performed with a medium beam size.
FIG. 21 illustrates a gel electrophoresis of a PCR reaction performed with a large beam size.
FIG. 22 illustrates a gel electrophoresis of PCR reactions carried out with varying beam size, S is a small sized beam, M is a medium sized beam, and L is large sized beam.
Figure 23:
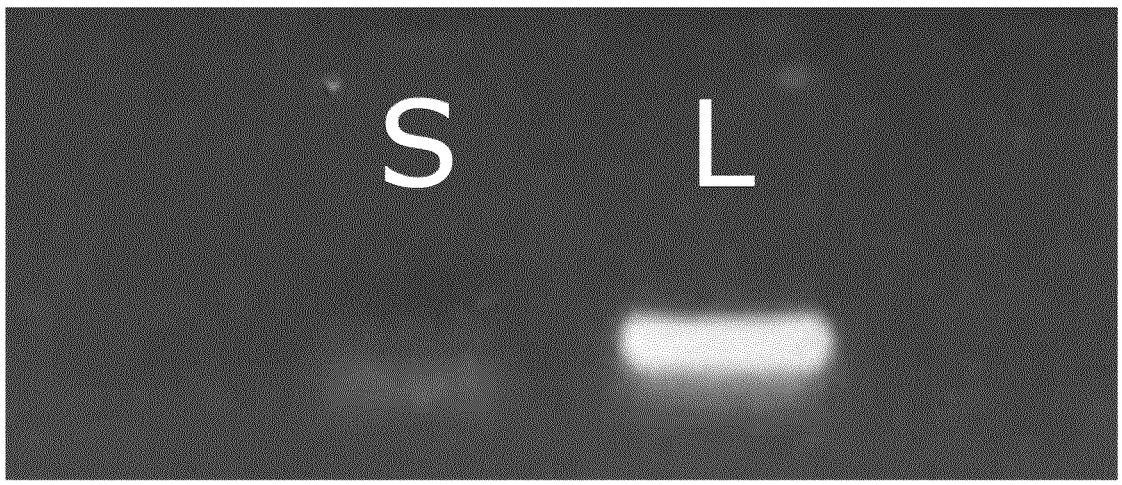
FIG. 23 illustrates a gel electrophoresis of PCR reactions carried out with varying beam size, S is a small sized beam, and L is large sized beam.

Next, the beam size was varied to see what effect this would have on our PCR product. As the total energy absorbed by the PCR mixture is independent of beam size, the same heating rate and total PCR time was achieved. The beams were varied from a large beam that covers the entire PCR tube, shown in FIG. 21, to a medium-sized beam that covers approximately 70 percent of it, shown in FIG. 20 and then finally focused to the smallest possible beam size for the gaussian beam, shown in FIG. 19. The PCR was performed with the optimized parameters with gel electrophoresis results shown in FIG. 22 and the second experiment with only a small beam and large beam shown in FIG. 23. It can be seen that if the beam is too small, very poor PCR efficiency is observed. This is most likely due to bad heat distribution when the beam is focused. Thus, one would want the beam size to be as large as possible while keeping all of the beam inside the tube.

4.5 Contact Heating Vs Non-Contact Heating Efficiency

Figure 24:
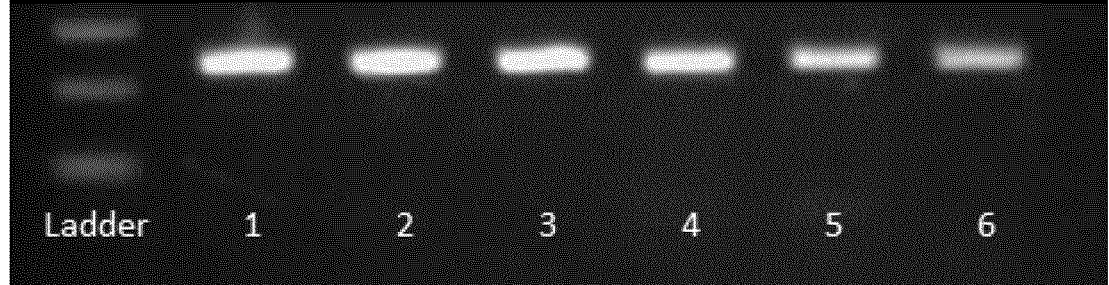
FIG. 24 illustrates a gel electrophoresis of contact gold nanorods PCR vs conventional PCR reactions. Lane 1 is Plasmonic PCR, $10^4$ per 20 μL CT DNA copies. Lane 2 is conventional PCR with $10^4$ per 20 μL CT DNA copies, with AuNR. Lane 3 is conventional PCR, $10^4$ per 20 μL CT DNA copies, without AuNR. Lane 4 is Plasmonic PCR, $10^3$ per 20 μL CT DNA copies. Lane 5 is conventional PCR, $10^3$ per 20 μL CT DNA copies, with AuNR. Lane 6 is conventional PCR, $10^3$ per 20 μL CT DNA copies, without AuNR.

Now that the system has been optimized, its PCR efficiency compared to that of the conventional PCR machines which use contact heating (Eppendorf Mastercycler Nexus Thermal Cycler) was investigated. The gel electrophoresis results are shown in FIG. 24. It can be seen that the efficiency is practically the same for all starting DNA concentrations. For the same hold time at all temperatures, the plasmonic system of the present invention took around 7 minutes, while the conventional PCR took 39 minutes.

EXAMPLE 5

Real Time Detection

As shown in FIG. 7, the change in transmission at 260 nm is being measured as free nucleotides are being turned into dsDNA. Using Beer-Lambert's law, the power measured by a photodetector after the UV-light has traveled through the medium before PCR has occurred follows the formula:

$$P_{measured_{pre}} = (1-\gamma L)P_{in}e^{-\mu_{dntp}c_{dntp}l} + \eta_1 \qquad \text{Eq. 6}$$

where $P_{measured\ pre}$ is the measured power prior to PCR, L is the loss factor, $P_{in}$ is the input power, $\mu_{dntp}$ is the extinction coefficient, $c_{dntp}$ is the starting concentration of dNTP, l is the optical path length and $\eta_1$ is the noise from detection in the pre PCR measurement of our system. After PCR has been completed, the measured power would be $$P_{measured_{post}} = (1-\gamma_L)P_{in}e^{-(F\mu_{dsna}c_{dntp}+(1-F)\mu_{dntp}c_{dntp})l} + \eta_2 \qquad \text{Eq. 7}$$

where F is the fraction of dNTP that has turned into DNA, and $\eta_2$ is the noise from detection post PCR. Dividing eq. (7) by eq. (6), and under the assumption of no noise being present in our system we would have the relative intensity to be $$P_{rel} = e^{Fc_{dntp}(\mu_{dntp}-\mu_{dsdna})l}, \qquad \text{Eq. 8}$$

we can thus track the fraction of dNTP that has been converted to dsDNA by inspecting the relative intensity. However, taking noise from the detection side into account the relative intensity becomes $$P_{rel_{noisy}} = \qquad \text{Eq. 9}$$

$$\frac{1}{\frac{1}{P_{rel}} + \frac{\eta_2 e^{\left(F\mu_{dsdna}c_{dntp}+(1-F)\mu_{dntp}c_{dntp}\right)l}}{(1-\gamma_L)P_{in}}} + \frac{\eta_1 e^{\mu_{dntp}c_{dntp}l}}{(1-\gamma_L)P_{in}} + \frac{\eta_2}{\eta_1}.$$

The first term in eq. (9), contains the noiseless relative power mixed with noise pre PCR.

The effect of noise pre and post PCR can be minimized by maximizing $P_{in}$ and having the loss factor, $\gamma L$ as small as possible.

Figure 25:
FIG. 25 illustrates a gel electrophoresis with varying dNTP concentration; dNTP concentration of lane 1 is standard 250 μM, lane 2 is 125 μM, lane 3 is 62.5 μM, lane 4 is 31.25 μM, lane 5 is 15.625 UM, and lane 6 is with standard 250 μM and no DNA template.

To get the largest relative change in intensity, $P_{rel\ noisless}$, one needs to get as much dNTP to convert to dsDNA as possible, i.e. getting F as close as possible to unity. This can be achieved by reducing the starting concentration of dNTP. However, reducing the dNTP concentration beyond a certain threshold will decrease PCR efficiency. By varying the starting concentration of dNTP, the extent to which dNTP concentration can be reduced without hindering our PCR's efficiency can be experimentally determined. The gel electrophoresis result of this is shown in FIG. 25. It can be seen that reduction in PCR efficiency starts to occur at concentrations lower than 62.5 µM. This concentration of dNTP shall be used for the experiments herein.

Figure 26:
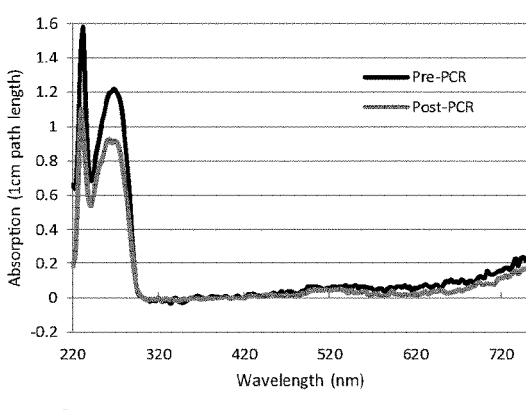
FIG. 26 illustrates the spectroscopy of varying dNTP concentrations.
Figure 26:
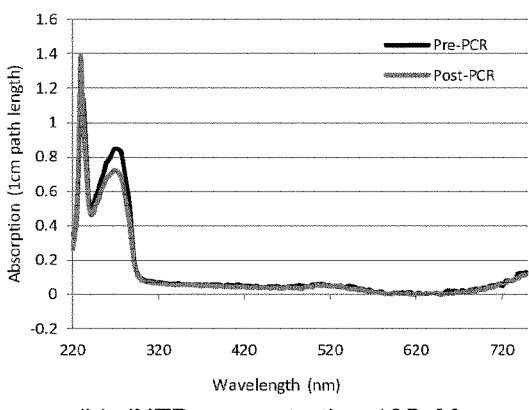
Figure 26:
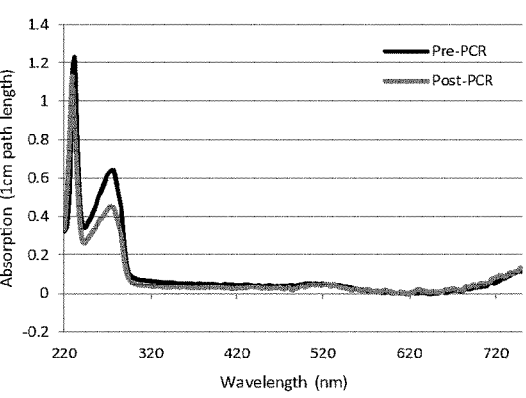
Figure 26:
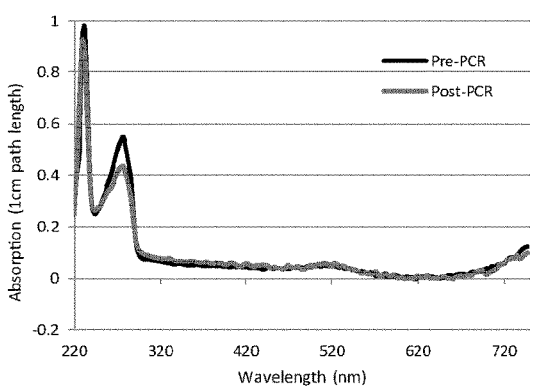
Figure 26:
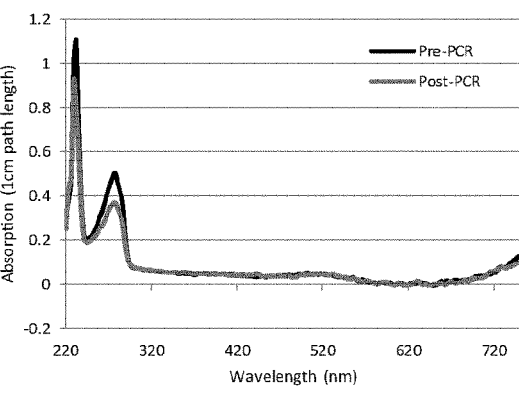
Figure 26:
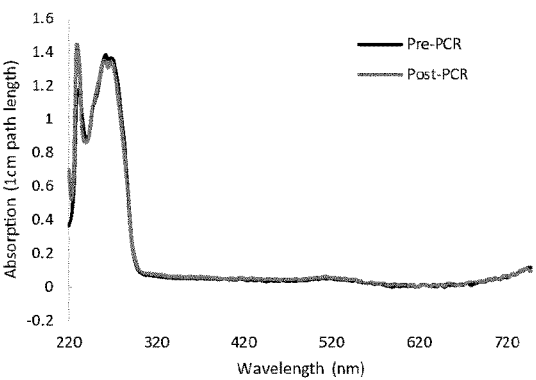

To verify the phenomenon summarized in table 4, the spectroscopy of the dNTP dilutions prior to PCR and post PCR was used; the results are shown in FIG. 26. It can be seen that because PCR has occurred in the first 5 lanes, there is a significant change in absorption in FIG. 26.

TABLE 4

| Change of extinction coefficient of nucleotides in free, ssDNA and dsDNA form | |
| --- | --- |
| | Average Extinction Coefficient at 260 nm |
| Free Nucleotides | 10750 M$^{-1}$cm$^{-1}$ |
| Nucleotides in ssDNA | 9675 M$^{-1}$cm$^{-1}$ |
| Nucleotides in dsDNA | 7062 M$^{-1}$cm$^{-1}$ |

5.1: UV-LED Drawbacks

Figure 27:
FIG. 27 illustrates a gel electrophoresis of PCR reactions carried out with varying exposure time, pre-PCR of 260 nm UV-LED 0.5 mW for 0 s, 5 s, 10 s, 20 s, 40 s, 80 s, 160 s, 320 s.
Figure 28:
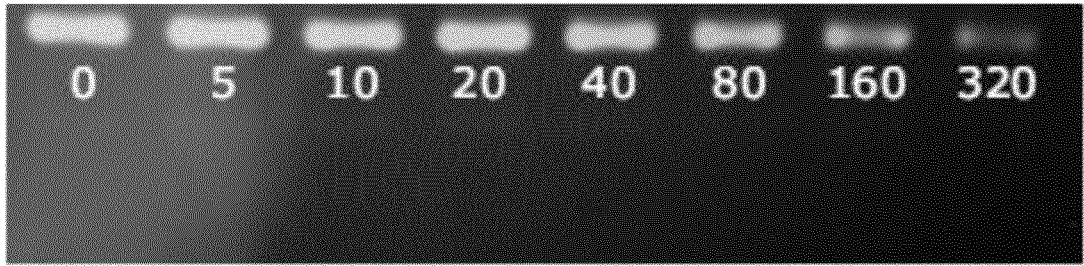
FIG. 28 illustrates a gel electrophoresis of PCR reactions carried out with varying exposure time, post-PCR of 260 nm UV-LED 0.5 mW for 0 s, 5 s, 10 s, 20 s, 40 s, 80 s, 160 s, 320 s.

As motioned previously, prolonged exposure of DNA to UV light can damage it enough that the formation of dsDNA is prevented, and thus no primer binding will occur with the damaged DNA. To determine how long can the solution can be exposed to UV light without it hindering PCR, the exposure time with the optical power of 0.5 mW was exponentially varied from 0 s to 320 s, before PCR and after PCR with the gel electrophoresis results shown in FIGS. 27 and 28. It can be seen that for both pre and post PCR UV exposure, an exposure time greater than 80 s will decrease the PCR yield. Assuming that one would wish to measure the transmission once every 35 cycles, this tells us that the exposure time per cycle must not exceed 80 s/35≈2.29 s.

5.2: Real Time Results

Figure 30:
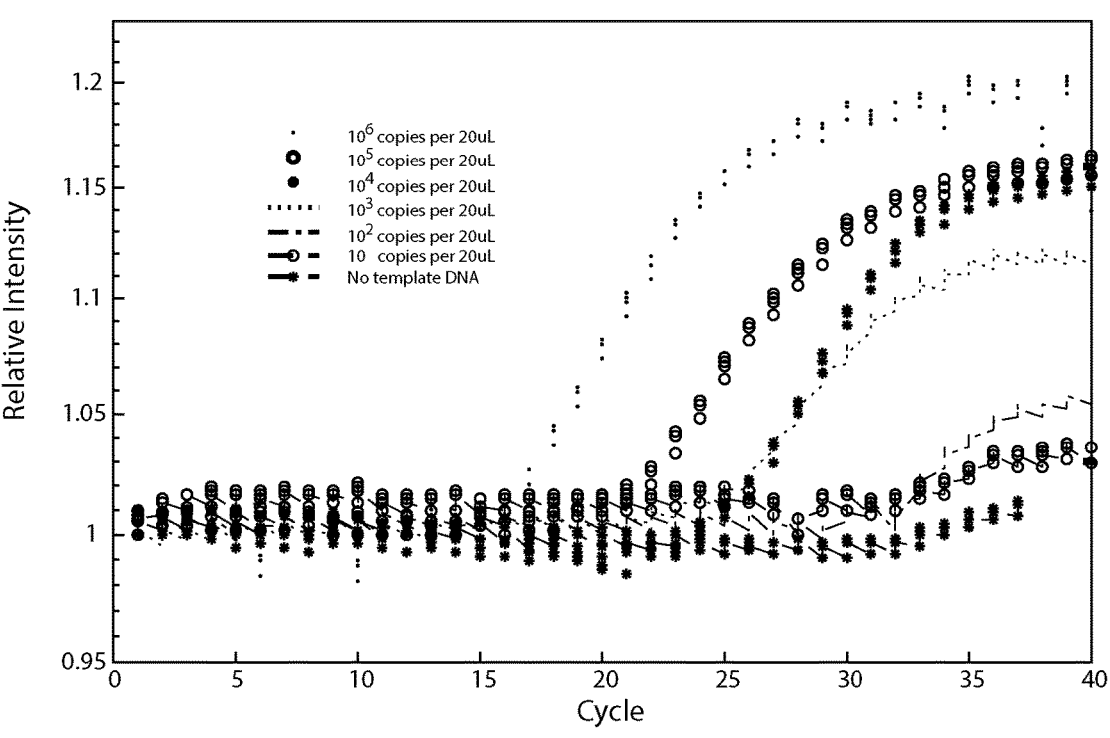
FIG. 30 illustrates the UV relative intensity vs cycle plot of PCR reactions performed with different starting DNA concentrations, and measured according to an embodiment of the present invention.

Real-time monitoring with a dNTP concentration of 62.5M was performed. The UV-LED is turned on for 30 ms at each cycle. The relative intensity for both a negative PCR with no template DNA and positive full PCR mix with different starting DNA concentration is shown in FIG. 30. Depending on the starting DNA concentration, the change in relative intensity reduces very slightly for a number of cycles at the beginning. This could be due to water evaporation in the solution, which causes an increase in concentration and thus, absorption. The more starting DNA concentration is present in the PCR mix, the earlier the change from dNTP to dsDNA reaches a detectable level and an exponential increase in relative intensity can be observed. For example, a positive change in power measured can be seen at 16 cycles for $10^6$ copies per 20 µL.

Figure 31:
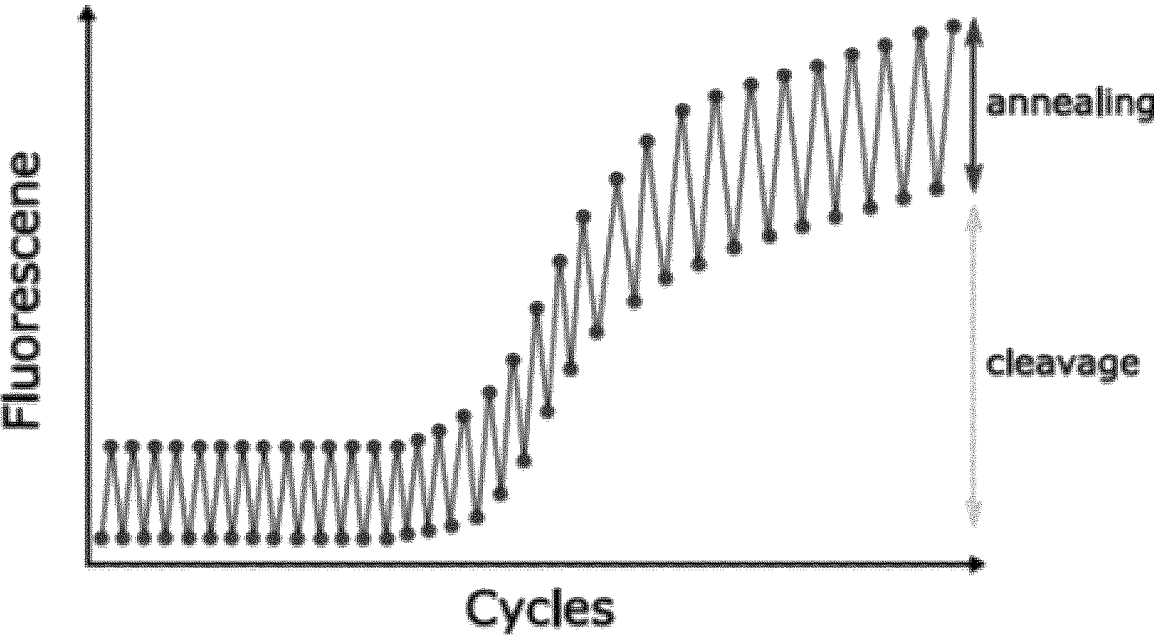
FIG. 31 is a visual representation of both probe annealing and cleavage occurring during a PCR reaction.

Once all the primers in the solution has either been extended to dsDNA or turned into primer dimers, further thermal cycling does not change the measured power. The point of saturation will appear earlier for higher starting DNA concentration. In fact, the plot of relative intensity (FIG. 30) is very similar to the fluorescent curves found in QPCR (FIG. 31). The gel electrophoresis results shown in FIG. 29 further assure us of the UV measurement results.

At a DNA template concentration of $10^3$ copies per 20 μL and lower, the changes in relative intensity are very similar. It was hypothesized that this is due to most of the primers forming primer-dimers instead of extending into the template DNA, as the primers are not incorporating into amplicons because of the low copy number. This hypothesis is confirmed after inspecting the intensity of the primer-dimer bands bellow our DNA product band in FIG. 29 of concentrations $10^3$ copies per 20 μL and less. With the results, the current limit of detection of the present invention appears to be around $10^3$ copies per 20 μL. Using eq. (8), the estimated fraction of dNTP that has been converted to DNA with different starting DNA concentrations is summarized in table 5.

TABLE 5

Fraction of dNTP converted to dsDNA, with different template DNA concentration.

| Template DNA (Copies/20 μL) | $10^6$ | $10^5$ | $10^4$ | $10^3$ | $10^2$ | 10 |
|---|---|---|---|---|---|---|
| F | 0.937 | 0.820 | 0.785 | 0.625 | 0.295 | 0.191 |

Figure 33:
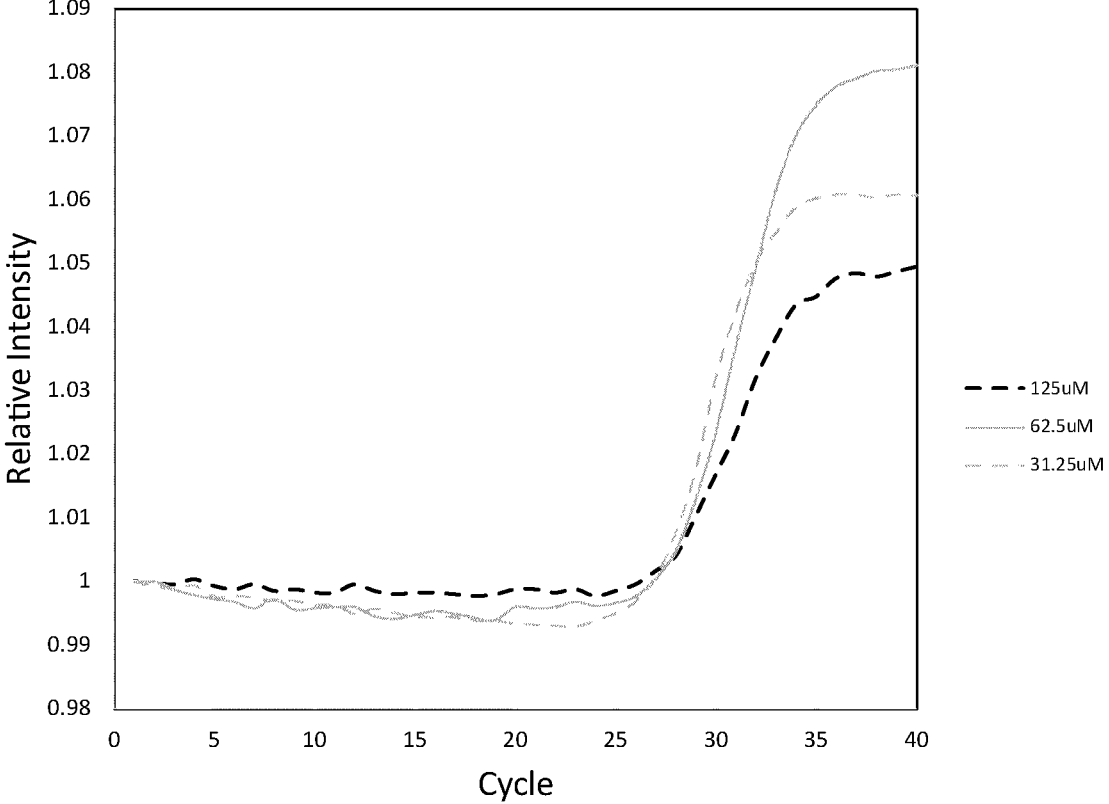
FIG. 33 illustrates real-time UV monitoring using different final concentrations of dNTPs; 125 μM, 62.5 μM, 31.25 μM.

Now referring to FIG. 33, which shows real-time UV monitoring using different final concentrations of dNTPs. It can be seen that monitoring can be performed over a range of concentration of the dNTPs, with the optimal concentration appears to be about 62.5 μM.

Figure 32:
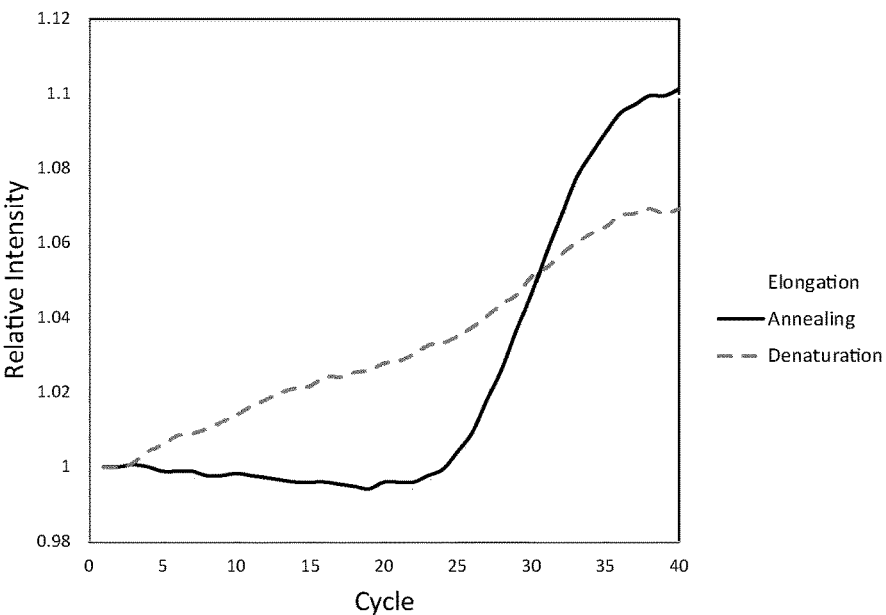
FIG. 32 illustrates real-time UV monitoring at denaturation, annealing and elongation stages of a (a) positive PCR, and (b) negative-No DNA template-PCR.
Figure 32:
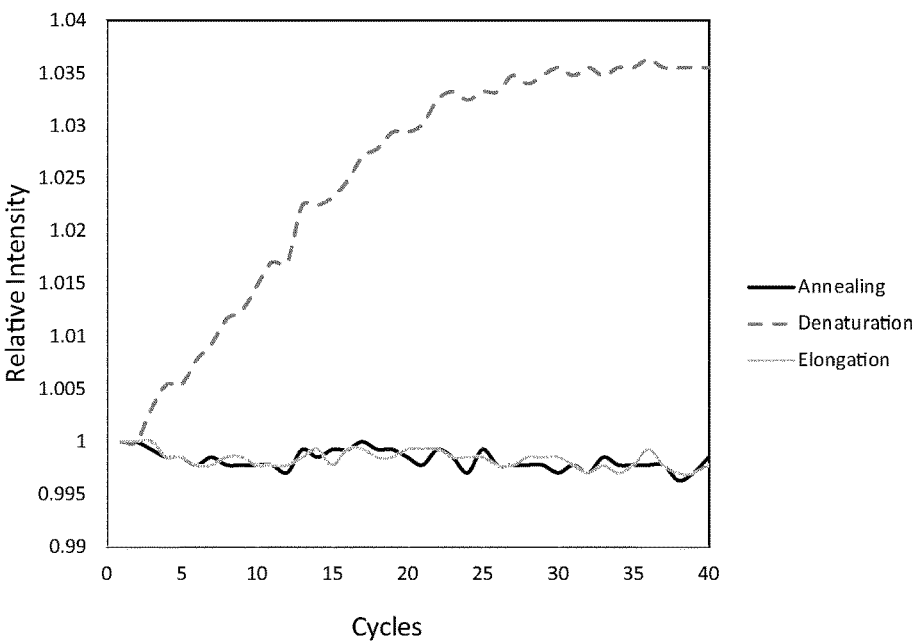
Figure 34:
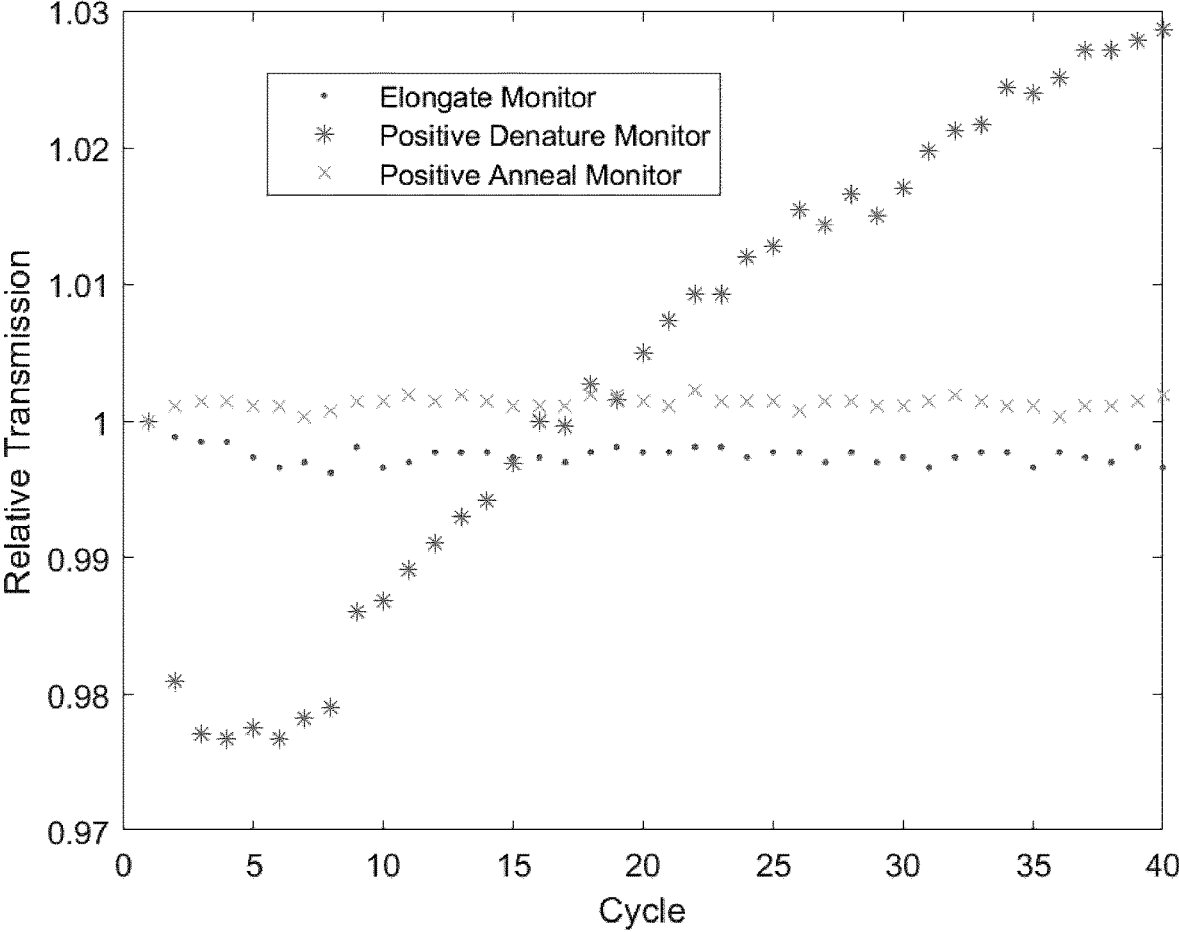
FIG. 34 illustrates real-time UV monitoring of reaction mixture only gold nanoparticles and PCR buffer.

Another critical illustration is referring to FIGS. 32 and 34, it can be seen that during the PCR cycle, real-time UV-monitoring can only be performed during annealing and elongation steps. Although UV-monitoring can differentiate between single stranded vs. double standard DNA, the monitoring at the denaturation stage when only single stranded DNA is present), is not ideal within the gold nanoparticle mixture. This can be seen by the increasing transmission changes at the denaturation step during the propagation of the reaction, whereas the transmission of at annealing and elongation steps are stable (FIG. 34).

Figure 35:
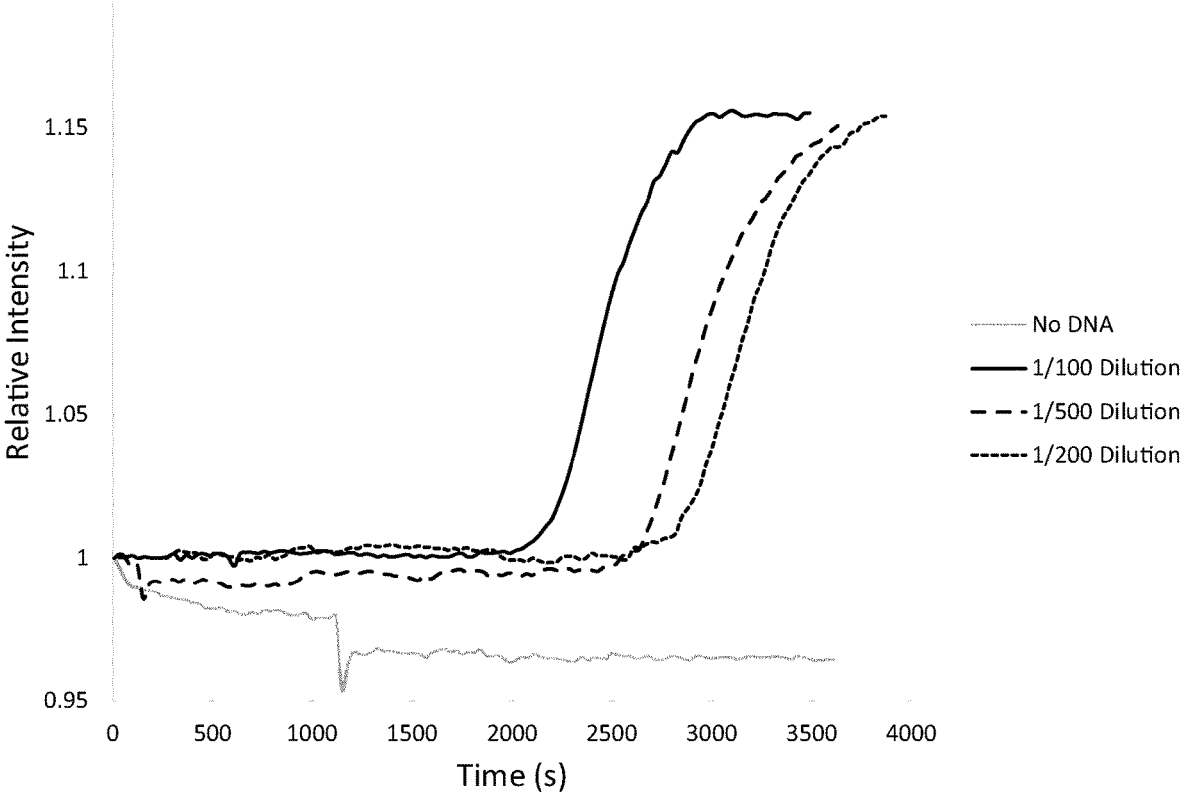
FIG. 35 illustrates real-time UV monitoring of a LAMP reaction mixture of a dilution series of *E. coli* HO157 serotype for *shigella* toxin 2 (stx2) gene.
Figure 36:
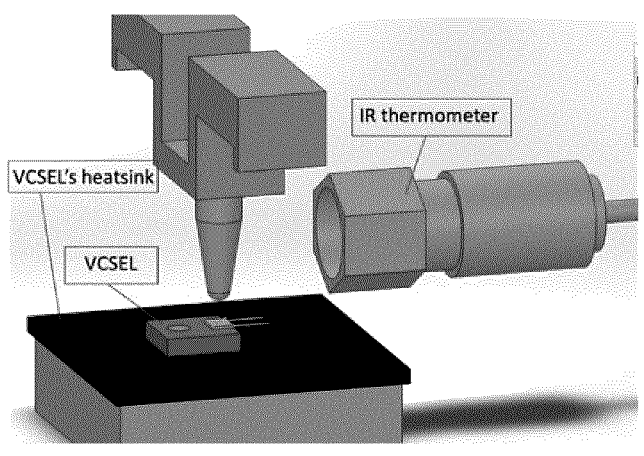
FIG. 36 illustrates a vertical-cavity surface-emitting lasers (VCSEL)-based PCR thermocycler according to an embodiment of the present invention.

Now referring to FIG. 35, which illustrates the real-time UV monitoring of a LAMP reaction mixture of a dilution series of *E. coli* HO157 serotype for shigella toxin 2 (stx2) gene. It can be seen that during the LAMP amplification, real-time UV-monitoring can also be performed during annealing and elongation steps. LAMP does involve an annealing and elongation step, but it does not involve cycling in the same manner as a PCR reaction. Therefore, in embodiments, UV monitoring of the LAMP reaction may be performed a predetermined time intervals, such as every minute or less, as may be necessary and the time of irradiation with the UV-LED may be for a duration from about 10 to 1000 ms, with 30 ms being sufficient. Also, the intensity may be from about 0.5 to about 1 mW, each cycle.

EXAMPLE 6

Point of Care (POC) PCR Device

One challenge of a POC PCR device is its power requirement, which may not be available in many developing world POC locations. In prior art devices, the laser diode system may have a total power consumption of about 30 W, if the optical output power is set at 2 W. Also, other system components will increase the total power consumption. Table 6 below Table shows the total dissipated energy for 40-cycle PCR based on the average time intervals ($T_{ON}$) that laser, fan, UV LED, and photodetector operate in the system.

Thus, one goal is to minimize this dissipated energy to arrive at a design for a potential portable battery-powered POC PCR device. One solution is to use another laser with higher power conversion efficiency or slope efficiency. For instance, high optical power vertical-cavity surface-emitting lasers (VCSEL) have approximately 40% wall plug efficiency, and if the VCSEL's optical output power is 3 W, the consumed electrical input power is given by eq. (10).

$$\text{Power Consumption } (W) = \frac{\text{Optical Output Power}}{\text{Wall Plug efficiency}} = \frac{3\ W}{0.4} = 7.5\ W \qquad \text{Eq. 11}$$

If it is assumed that the VCSEL-based plasmonic thermocycler has the same heating rate as the previous studies, the total dissipated energy for 40 cycles is 25% less than diode laser system. This power consumption can be further reduced if faster heating rate is achieved.

TABLE 6

Estimated power consumption of real-time plasmonic PCR

| Name | Supplier | Power Consumption (W) | $T_{ON}$ (s) | Total dissipated Energy (J) |
|---|---|---|---|---|
| LRD-0808 Collimated Diode Laser System | LaserGolw | 30 | 306.81 | 9204.3 |
| Thermometer Probe | Optris | 0.02 | 664 | 13.28 |
| 12 V DC Fan | AVNET | 30 | 155.95 | 4678.5 |
| UV LED | Thorlabs | 0.001 | 1.4 | 0.0014 |
| GaP Switchable Gain Amplified Detector | Thorlabs | 5 | 1.4 | 7 |
| Total | | 65 | 1129.56 | 73445 |

6.1: Selection of Laser and its Optimal Positioning

In the present example, gold nanorods (GNR) are dispersed in PCR reaction mixture, and are irradiated with a laser at their resonance wavelength. Previous plasmonic thermocyclers cannot be used as POC devices due to the size of heating lasers and drivers. One way of overcoming this problem is to use compact lasers. Fibre-coupled laser and free-space VCSEL are preferable over free-space diode laser systems in the present application due to their compact form factor. The principal advantage of fibre-based design is the absence of a need for optical alignment and therefore their flexibility in positioning respective to the sample. Therefore, with the help of fibres, laser source can be placed far from the thermocycling system, and laser light may be directed easily on the PCR tube. Such a system with remotely-placed-laser source should require less thermal management, as the dissipated heat of the laser source will not impact the cooling rate inside the thermocycler. Also, free-space VCSELs have high coupling efficiency with proper positioning and optical alignment. Since in PCR procedure the minimum temperature is usually set at about 60° C., the dissipated heat of VCSEL should be negligible in comparison with the relatively "hot" PCR tube. This makes free-space VCSELs equally favorable as fibre-coupled lasers in the desired application. However, the only factor which makes fibre-coupled lasers less practical is the cost due to their packaging, particularly for the case of multi-well plasmonic PCR which requires efficient coupling of multiple laser arrays to optical fibres. Consequently, in the present plasmonic thermocycler, the VCSEL is placed as close as possible to the PCR tube, so that the maximum beam width couples into the PCR tube. Heating in this manner should enhance the laser light coupling efficiency as well as favor uniform heating inside the PCR reaction tube.

6.2: Optimal VCSEL Position

In order to have maximum heating rate, the laser should be placed in an optimal position, so that all the VCSEL's optical power couples into the PCR tube. Therefore, the free-space Gaussian beam propagation is analyzed for two different VCSEL-tube distances using Zemax non-sequential mode.

Figure 37:
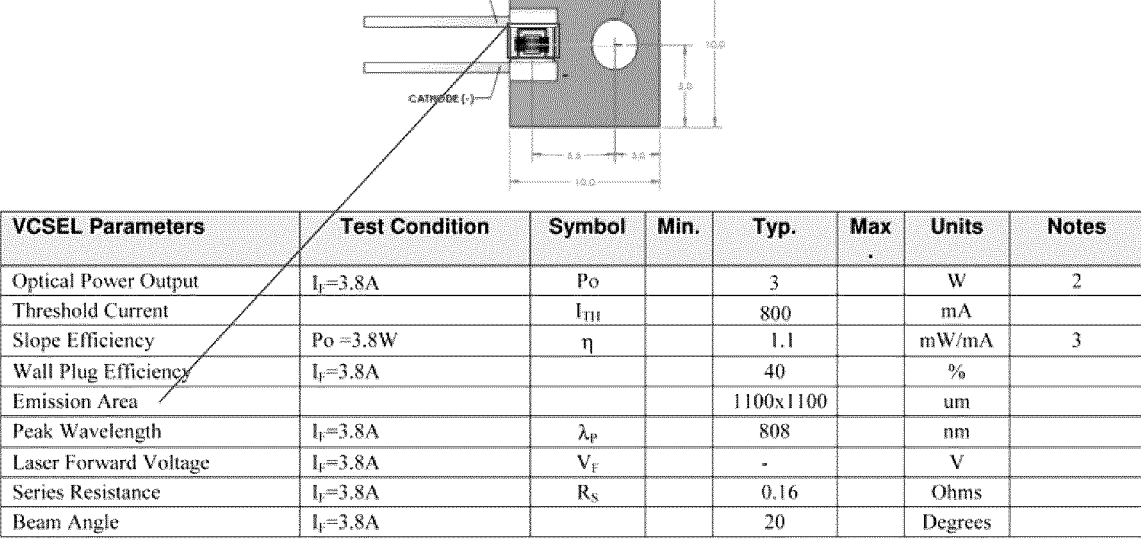
FIG. 37 illustrates the electro-optical characteristics of a VCSEL used in a VCSEL-based PCR thermocycler according to an embodiment of the present invention.
Figure 38:
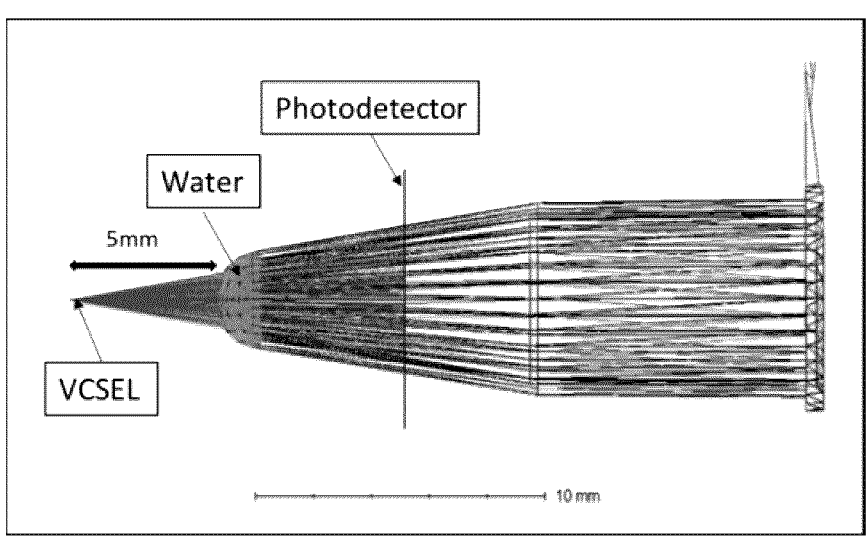
FIG. 38 illustrates the 5 mm VCSEL-tube distance layout.
Figure 39:
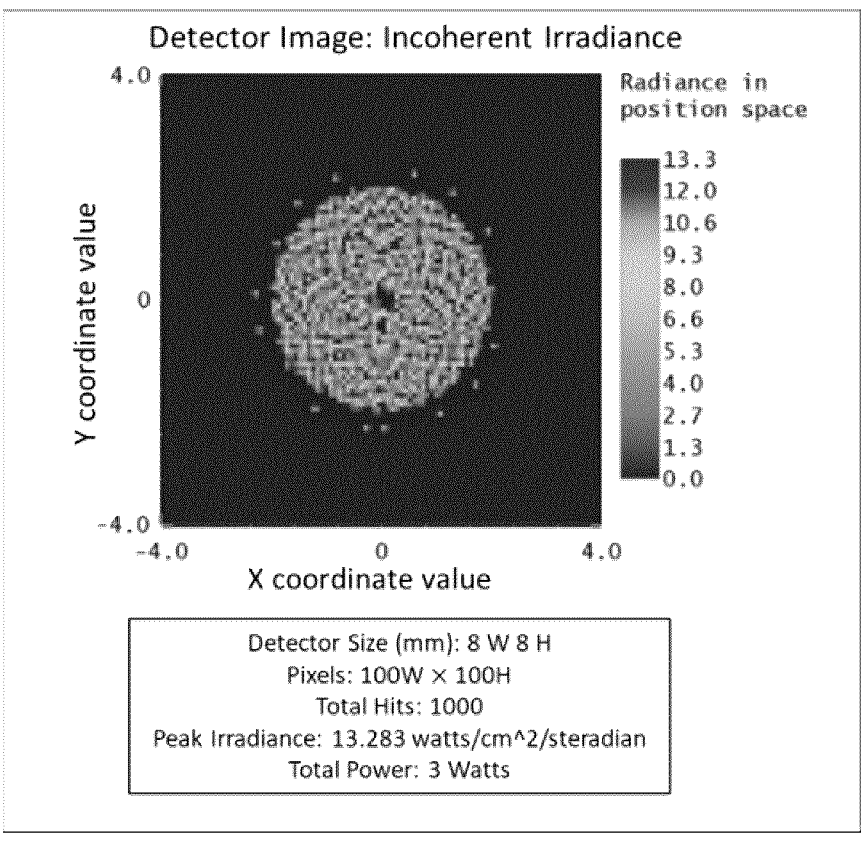
FIG. 39 illustrates the 3 W power received at the photodetector with no loss.

In the first scenario, the laser is placed slightly more than 5 mm below the tube and the source is modeled such that it has a Gaussian distribution of rays which appear to emanate from a point source. The beam waist is assumed to be 1.1 mm, which is roughly equal to the emission length of the VCSEL shown in FIG. 37. The beam waist is located close to point source, so that the distance from the beam waist to tube is 5 mm. The refractive index of the plastic tube is set to 1.49 with respect to beam wavelength, and water is considered as the PCR solution inside the tube. In this model, the absorption and scattering events in PCR solution are ignored since only the optimal VCSEL's position for better beam coupling was the main objective. FIGS. 37 and 38 shows that the total optical power of VCSEL (3 W with 3.8 amp of continuous forward current) is received at photodetector with 5 mm VCSEL-tube distance.

Figure 40:
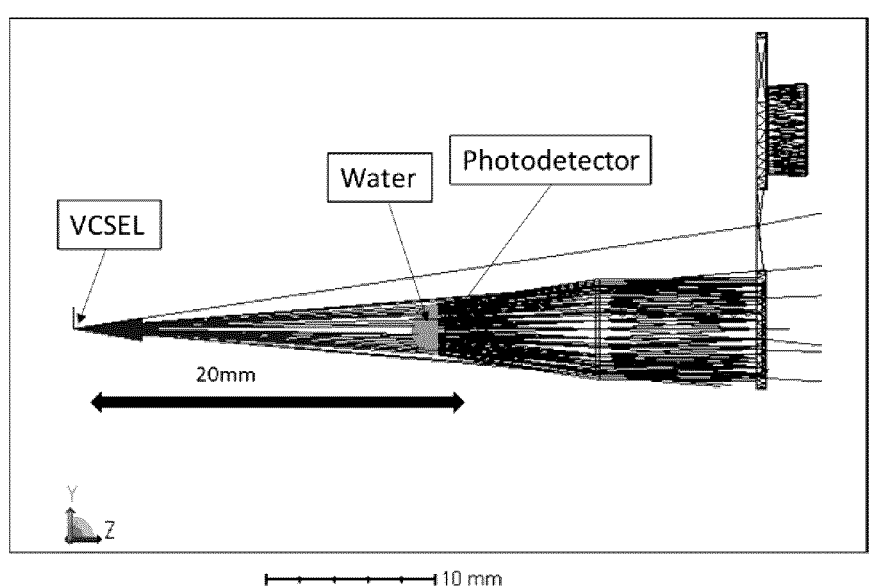
FIG. 40 illustrates the 20 mm VCSEL-tube distance layout.
Figure 41:
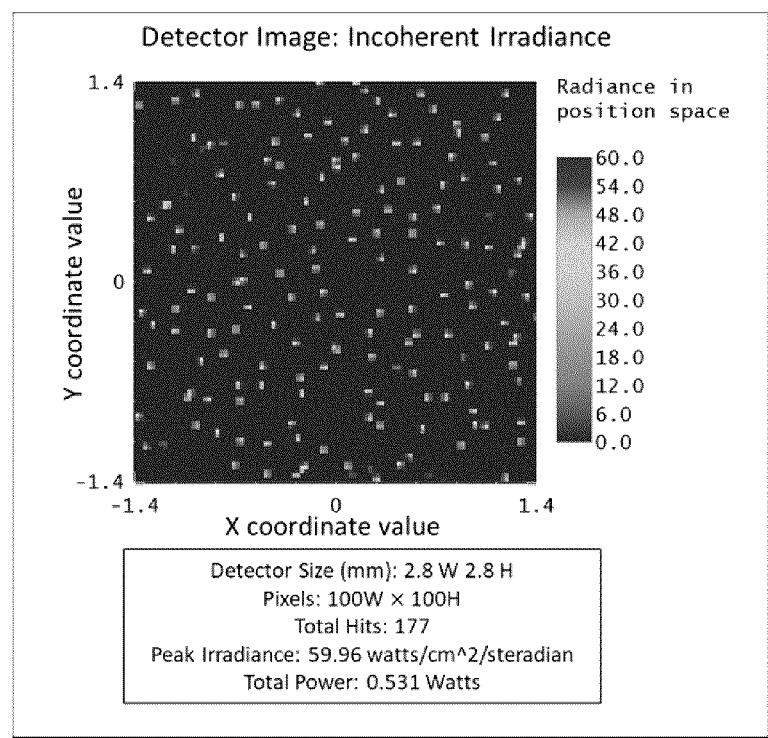
FIG. 41 illustrates that 17.7% of the VCSEL 3 W power received at the photodetector.

For the second scenario, the VCSEL-tube distance is 20 mm (FIG. 40), and it is shown in FIG. 41 that 82.3% of optical power is lost at detection site due to beam divergence. At a 20 mm VCSEL-tube distance, the PD's size was reduced intentionally to resemble the water dimensions inside the tube.

Figure 29:
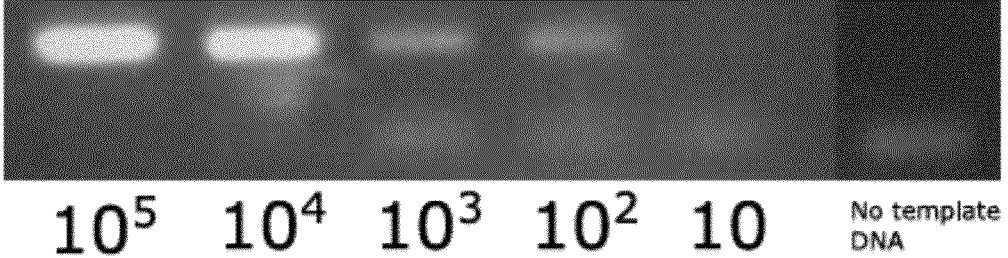
FIG. 29 illustrates a confirmation gel electrophoresis of PCR reactions carried out and UV measured according to an embodiment of the present invention.
Figure 42:
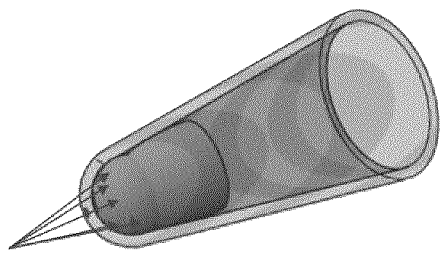
FIG. 42 illustrates the laser light contacting the enzymatic reaction mixture in a tube (top) and the laser light confinement on the surface of the tube with 10 mm distance from the VCSEL (bottom).
Figure 42:
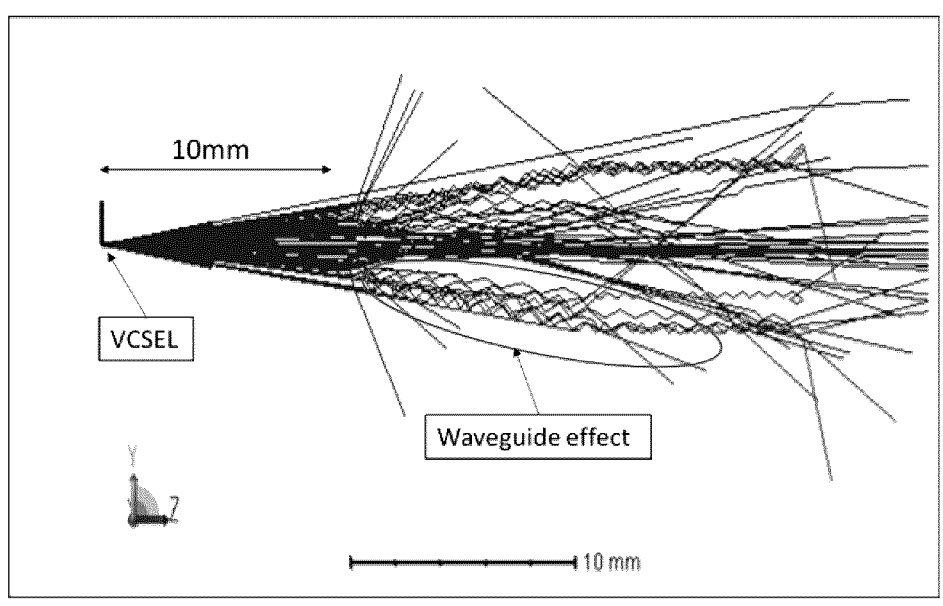
Figure 43:
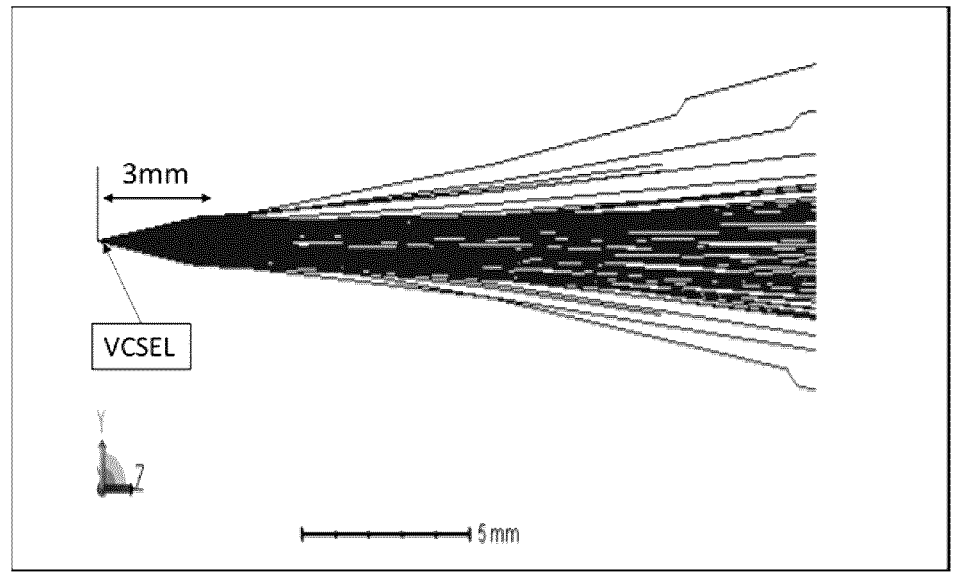
FIG. 43 illustrates that there is no waveguide effect with 3 mm VCSEL-tube distance.

Moreover, the plastic tube and PCR sample have an approximate refractive index ($n_{\lambda 208}$) of 1.49 and 1.33 at 808 nm wavelength respectively. The $n_{\lambda 808}$ of water is assigned to PCR mixture since more than half of PCR sample's volume is water. As a plastic tube with higher $n_{\lambda 808}$ is between two media of lower $n_{\lambda 808}$ c (PCR solution and air), light propagates in the tube wall instead of being coupled into the PCR sample. FIG. 42, bottom shows the total internal reflections (waveguide effect) on the surface of tube with 10 mm VCSEL-tube distance. This can be avoided by proper positioning of the VCSEL with respect to tube which is shown in FIG. 29. The tube is not drawn in FIG. 28 and FIG. 29 to make the ray tracing more visible. Consequently, for the present design, placement of the VCSEL at about 3 to about 5 mm from the tube to enhance coupling efficiency and avoid waveguide effect.

6.3:30 Cycles Under 10 Minutes

Figure 44:
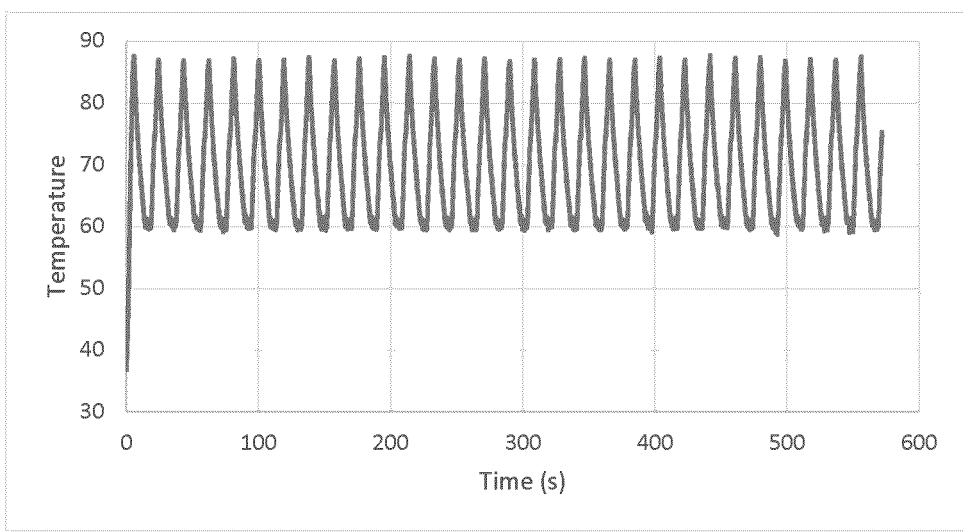
FIG. 44 illustrates the VCSEL-based thermocycling curve of 30 cycles in sub ten-minute, according to an embodiment of the present invention.
Figure 45:
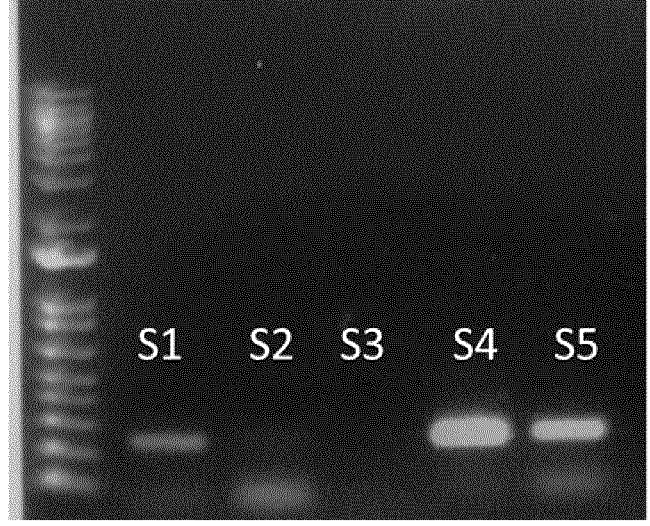
FIG. 45 illustrates gel electrophoresis image for comparing plasmonic and conventional PCR assay. S1: Plasmonic-Negative Control (No DNA; S2: Plasmonic-Negative Control (No Polymerase); S3: Conventional-Negative Control (No DNA); S4: Conventional-Positive Control; and S5: Plasmonic-Positive Control.

The thermocycling curve for 30 cycles of PCR amplification using a VCSEL-based system is shown in FIG. 44. A less than ten-minute amplification time is achieved with the help of a 3 W VCSEL and PEG-GNRs, and the heating and cooling rates of 6.64° C./s and 3.1° C./s respectively. The result of this plasmonic platform is compared with a conventional PCR machine (Eppendorf Mastercycler Nexus™ Thermal Cycler) by running gel electrophoresis. The gel image. FIG. 45 shows that our VCSEL-based thermal cycler produced the same amount of dsDNA fold change as the conventional PCR.

6.4: Annealing Hold-Time, Cooling Rate, and Fan Speed Optimization

Samples with the same PCR ingredient's concentration were prepared, and different annealing hold-times, cooling rates, and fan speeds were tested on them. Table shows these different scenarios.

Annealing hold-time: S1 to S3 shows that annealing hold-time less than 5 s results in PCR failure. Thus, in all experiments an annealing hold-time for 5 s is used.

Oil Volume: S4 experimented with less oil volume for better heat dissipation during sample cooling, which results in PCR failure. Volumes between 25 to 50 µl would likely improve performance.

Figure 46:
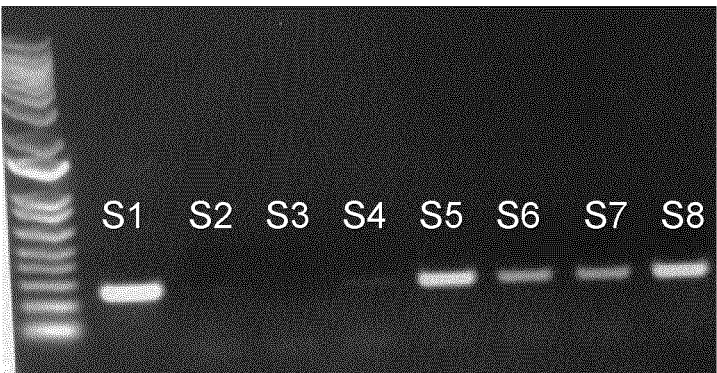
FIG. 46 illustrates gel electrophoresis image for comparing plasmonic entional PCR assay conditions. Sample legend may be found in Table 7.

Fan speed: The 14V DC fan with maximum air flow of 15.32 CFM and speed of 4400 R.P.M provides cooling rate of 3.1° C./s. As the DC voltage applied to fan is varied, its speed and air flow also change. Therefore, we applied different fan voltages to increase cooling rates and performed a 40-cycle PCR on samples from the same PCR stock solution. Sample 5 and 6 in FIG. 46 show that PCR efficiency is reduced for 16 and 18 fan voltages corresponding to cooling rates of 4.1 and 5° C./s due to thermal lag between GNRs and PCR liquid and consequently unannealed primers. However, sample 8 shows even with fan at 18V, the PCR was successful by lowering the annealing temperature. This 3° C. drop in annealing temperature allows enough time to GNRs to dissipate heat and primers to anneal, but high cooling rate with lower annealing temperature is not favorable since running the fan at higher speed for longer time to reach a lower temperature is required. Finally, for all experiments, a 14V fan, 5 s annealing hold-time, and 50 µl mineral oil may be used.

TABLE 7

Experiments on different fan speeds, annealing temperatures, and oil volume

| Sample No. | Fan Voltage (V) | Cooling rate (° C./s) | Annealing hold-time (s) | Annealing Temp. (° C.) | Oil Volume (µl) |
|---|---|---|---|---|---|
| S1 | 14 | 3.1 | 5 | 60 | 50 |
| S2 | 14 | | 2.5 | 60 | 50 |
| S3 | 14 | | 3.5 | 60 | 50 |
| S4 | 14 | | 5 | 60 | 25 |
| S5 | 16 | 4.1 | 5 | 60 | 50 |
| S6 | 18 | 5 | 5 | 60 | 50 |
| S7 | 18 | | 5 | 63 | 50 |
| S8 | 18 | | 5 | 57 | 50 |

EXAMPLE 7

UV Monitoring with Optical Design Comprising a Light Pipe

To test for high sensitivity DNA detection, even for minimal optical intensity changes at PD, a fused silica light pipe may be used. This design is simulated in an optical design program called Zemax to compare its efficiencies.

Figure 47:
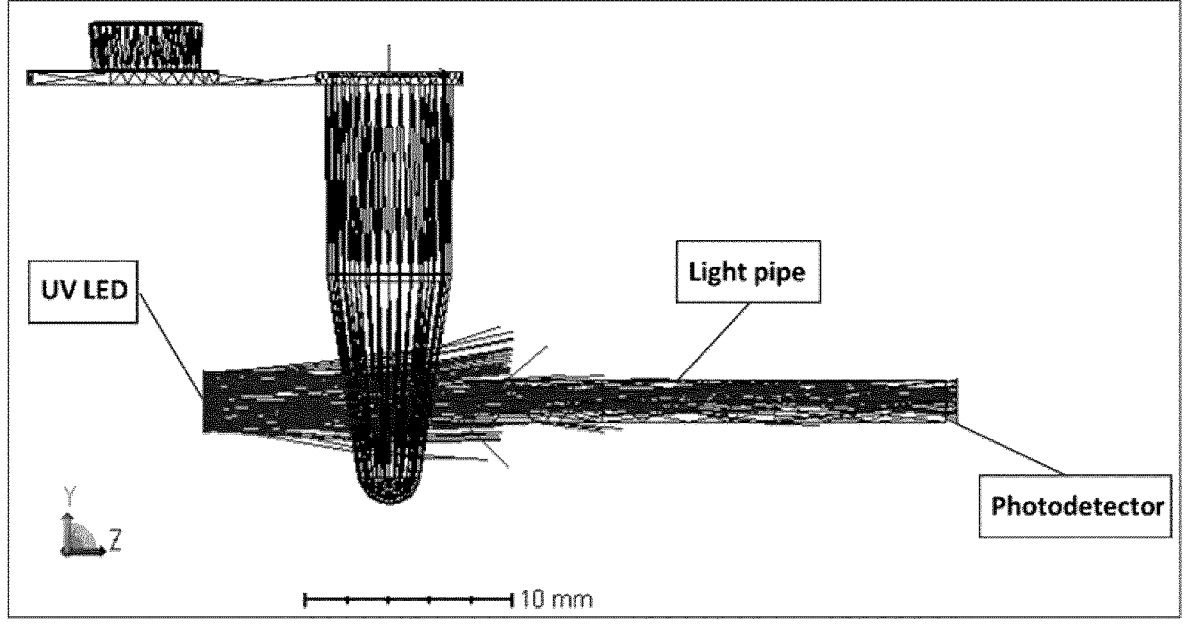
FIG. 47 illustrates a UV monitoring system with a light pipe according to an embodiment of the present invention.
Figure 48:
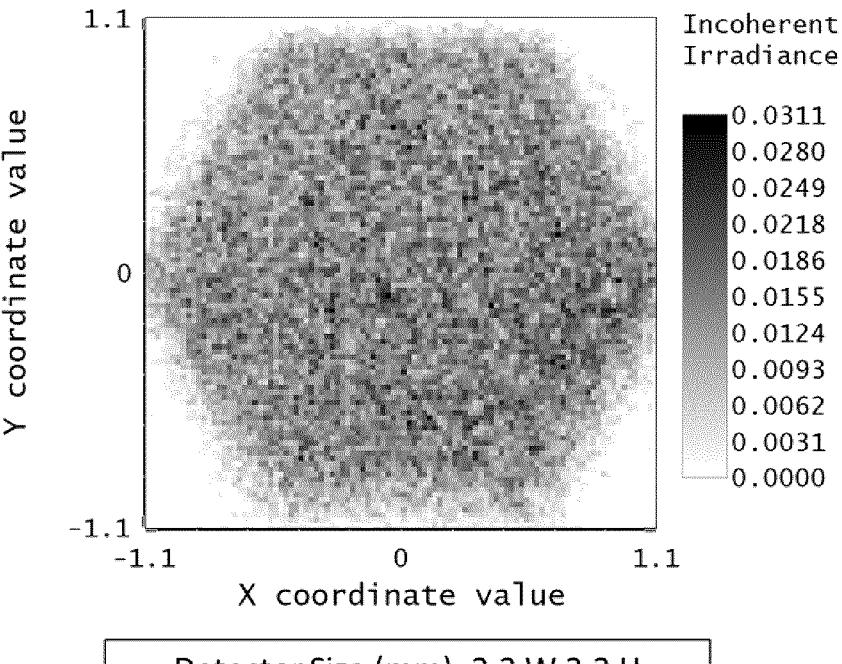
FIG. 48 illustrates the irradiance view at the photodetector from a simulation of system with a light pipe according to an embodiment of the present invention, and showing that 94.7% of UV LED light power reaches the PD with a light pipe.

Considering an active area of the PD of 4.8 mm², light pipe with less than 2.5 mm exit aperture are an appropriate choice to direct light on the PD. However, the entrance aperture depends on the beam coming out of PCR tube. As shown in FIG. 47, the design simulates uses a 2 mm entrance and exit aperture fused silica light pipe (e.g. from Edmund Optics™) placed between UV LED and PD, but after the PCR tube. In FIG. 48, it is shown that 94.7% of UV LED power reaches the PD with a light pipe.

While preferred embodiments have been described above and illustrated in the accompanying drawings, it will be evident to those skilled in the art that modifications may be made without departing from this disclosure. Such modifications are considered as possible variants comprised in the scope of the disclosure.

The invention claimed is:

1. A method of amplifying a nucleic acid molecule and quantifying amplification thereof, of a nucleic acid template with a polymerase chain reaction (PCR) or a loop-mediated isothermal amplification (LAMP), the method comprising:

a) performing said PCR or said LAMP and during said PCR or said LAMP, irradiating a biological enzymatic reaction mixture in solution, for a period of time sufficient, with a heating activation light beam from a continuous wave laser, said biological enzymatic reaction mixture comprising said nucleic acid template, a polymerase enzyme and chemically modified nanoparticles comprising nanorods of metal, said heating activation light beam having a wavelength resonant with a surface plasmon of said chemically modified nanoparticles, which activates a plasmon resonance localized at a surface of said chemically modified nanoparticles, which causes a release of heat sufficient to heat a whole of said biological enzymatic reaction mixture and promote said PCR or said LAMP, b) irradiating said biological enzymatic reaction mixture with a monitoring ultraviolet (UV) light from an UV light source during an annealing step, an elongation step, or both, of said PCR or said LAMP, and c) measuring with a photodetector a transmission change in an UV light transmission from said biological enzymatic reaction mixture to quantify amplification of said nucleic acid template, wherein irradiating with said monitoring UV light from an UV light source is for a duration and at an UV light intensity sufficient for measuring said transmission change to measure a free nucleotide concentration to quantify amplification of said nucleic acid template in said biological enzymatic reaction mixture, while avoiding inhibition of amplification of said nucleic acid template.

2. The method of claim 1, wherein said PCR is a reverse transcriptase (RT) PCR, or said LAMP is a RT LAMP.

3. The method of claim 1, wherein said nanorods of metal are selected from the group consisting of nanorods of Au, Ag, Pd, Pt, Fe, Cu, Al, and Zn.

4. The method of claim 1, wherein said chemically modified nanoparticles comprise a surface modification with a chemical compound that prevents association with an active site of said polymerase enzyme and inhibits the polymerase activity of said polymerase enzyme.

5. The method of claim 4, wherein said chemical compound is polyethylene glycol.

6. The method claim 1, wherein in step a) said irradiating with a heating activation light beam from a continuous wave laser comprises adjusting a power of said activation light beam to regulate a temperature of said biological enzymatic reaction mixture by controlling said release of heat from said chemically modified nanoparticles.

7. The method of claim 1, wherein said continuous wave laser is a fibre-coupled laser, a vertical-cavity surface-emitting laser (VCSEL), or a combination of said fibre-coupled laser and said VCSEL.

8. The method of claim 1, wherein said activation light beam from said continuous wave laser is provided from a distance of ≤5 mm from said biological enzymatic reaction mixture.

9. The method of claim 1, further comprising a step of optically monitoring a temperature change of said biological enzymatic reaction mixture.

10. The method of claim 9, wherein said optically monitoring is performed with an infrared thermometer.

11. The method of claim 9, wherein said optically monitoring is during said annealing step or during said elongation step.

12. The method of claim 1, wherein said duration is from 10 ms to 1000 ms.

13. The method of claim 1, wherein said UV light source emits light having a wavelength of from 175 nm to 350 nm.

14. The method of claim 1, wherein UV light from said UV light source is focused through an optical lens, a light pipe, or a combination of said optical lens and said light pipe.

15. The method of claim 1, wherein said quantifying amplification of said nucleic acid template is performed in real-time.

* * * * *